US009433895B2

(12) United States Patent
Yu et al.

(10) Patent No.: US 9,433,895 B2
(45) Date of Patent: Sep. 6, 2016

(54) REVERSIBLE ROOM-TEMPERATURE IONIC LIQUIDS

(71) Applicant: Georgetown University, Washington, DC (US)

(72) Inventors: Tao Yu, Arlington, VA (US); Richard G. Weiss, Bethesda, MD (US); Taisuke Yamada, Arlington, VA (US); Mathew George, Newark, DE (US)

(73) Assignee: Georgetown University, Washington, DC (US)

( * ) Notice: Subject to any disclaimer, the term of this patent is extended or adjusted under 35 U.S.C. 154(b) by 219 days.

(21) Appl. No.: 14/072,439

(22) Filed: Nov. 5, 2013

(65) Prior Publication Data

US 2014/0120013 A1 May 1, 2014

Related U.S. Application Data

(63) Continuation of application No. 12/524,639, filed as application No. PCT/US2008/052161 on Jan. 28, 2008, now Pat. No. 8,574,453.

(60) Provisional application No. 60/898,116, filed on Jan. 29, 2007.

(51) Int. Cl.

| | |
|---|---|
| ***B01D 53/62*** | (2006.01) |
| ***B01D 53/78*** | (2006.01) |
| ***B01D 53/14*** | (2006.01) |
| ***B01D 53/96*** | (2006.01) |
| ***C01B 31/16*** | (2006.01) |
| ***C09K 3/00*** | (2006.01) |
| ***C07C 213/08*** | (2006.01) |
| ***C07C 257/14*** | (2006.01) |
| ***C07C 271/02*** | (2006.01) |
| ***C07C 319/20*** | (2006.01) |
| ***C07C 323/43*** | (2006.01) |
| ***C07D 487/04*** | (2006.01) |

(52) U.S. Cl.

CPC ........... *B01D 53/62* (2013.01); *B01D 53/1493* (2013.01); *C07C 213/08* (2013.01); *C07C 257/14* (2013.01); *C07C 271/02* (2013.01); *C07C 319/20* (2013.01); *C07C 323/43* (2013.01); *C07D 487/04* (2013.01)

(58) Field of Classification Search

None

See application file for complete search history.

(56) References Cited

U.S. PATENT DOCUMENTS

2004/0035293 A1 2/2004 Davis

OTHER PUBLICATIONS

Yamada et al., "Reversible, Room-Temperature Ionic Liquids. Amidinium Carbmaates Derived from Amidines and Aliphatic Primary Amines with Carbon Dioxide." Chem. Mater. (2007), vol. 19, pp. 967-969 (published on Web on Feb. 6, 2007).*

Jessop, P.G. et al., "Reversible Nonpolar-to-Polar Solvent," *Nature*, 436:1102 (2005).

(Continued)

*Primary Examiner* — Daniel Berns

(74) *Attorney, Agent, or Firm* — Dana M. Gordon; Foley Hoag LLP

(57) ABSTRACT

One aspect of the present invention relates to salts that are room-temperature ionic liquids (RTILs), methods of making them, and methods of using them in connection with temporary or permanent gas sequestration. Another aspect of the present invention relates to a class of solvents which can be transformed into RTILs by exposure to a gas, and methods of using them in connection with temporary or permanent gas sequestration.

11 Claims, 20 Drawing Sheets

DBU n DBUn-C

L n Ln-C

| L | R | L | R | n | R' | n | R' |
|---|---|---|---|---|---|---|---|
| A | $n$-$C_4H_9$ | D | $n$-$C_7H_{15}$ | 1 | $n$-$C_4H_9$ | 5 | $n$-$C_6H_{13}$ |
| B | $n$-$C_5H_{11}$ | E | $n$-$C_8H_{17}$ | 2 | $sec$-$C_4H_9$ | 6 | $n$-$C_8H_{17}$ |
| C | $n$-$C_6H_{13}$ | | | 3 | $t$-$C_4H_9$ | 7 | $-C_2H_4NH_2$ |
| | | | | 4 | cyclohexyl | 8 | $-C_6H_{12}NH_2$ |

(56) References Cited

OTHER PUBLICATIONS

Liu, Y. et al., "Switchable Surfactants," *Science*, 313:958-960 (2006).
Phan, L. et al., "Switchable-Polarity Solvents Prepared with a Single Liquid Component", *J. Org. Chem.*, 73:127-132 (2008).
Yamada, T. et al., "Reversible, Room-Temperature, Chiral Ionic Liquids, Amidinium Carbamates Derived from Amidines and Amino-Acid Esters with Carbon Dioxide", *Chem. Mater.*, 19:4761-4768 (2007).
International Search Report for PCT/US08/052161 mailed Jun. 9, 2008.

* cited by examiner

DBU n DBUn-C

L n Ln-C

| L | R | L | R |
|---|---|---|---|
| A | *n*-$C_4H_9$ | D | *n*-$C_7H_{15}$ |
| B | *n*-$C_5H_{11}$ | E | *n*-$C_8H_{17}$ |
| C | *n*-$C_6H_{13}$ | | |

| n | R' | n | R' |
|---|---|---|---|
| 1 | *n*-$C_4H_9$ | 5 | *n*-$C_6H_{13}$ |
| 2 | *sec*-$C_4H_9$ | 6 | *n*-$C_8H_{17}$ |
| 3 | *t*-$C_4H_9$ | 7 | -$C_2H_4NH_2$ |
| 4 | cyclohexyl | 8 | -$C_6H_{12}NH_2$ |

Figure 2

| amine | 1 | | 2 | | 3 | | 4 | | 5 | | 6 | | 7 | | 8 | |
|---|---|---|---|---|---|---|---|---|---|---|---|---|---|---|---|---|
| amidine | *B* | *A* | *B* | *A* | *B* | *A* | *B* | *A* | *B* | *A* | *B* | *A* | *B* | *A* | *B* | *A* |
| dried **DBU** | *l* | *l* | *l* | *l* | *l* | *s* | *l* | *l* | *l* | *l* | *l* | *l* | *l* | *l* | *m* | *s* |
| **A** | *l* | *l* | *l* | *l* | *l* | *s* | *l* | *l* | *l* | *l* | *l* | *m* | *l* | *m* | *m* | *s* |
| **B** | *l* | *l* | *l* | *l* | *l* | *s* | *l* | *s* | *l* | *l* | *l* | *l* | *l* | *m* | *m* | *s* |
| **C** | *l* | *l* | *l* | *l* | *l* | *s* | *l* | *s* | *l* | *l* | *l* | *m* | *l* | *m* | *m* | *s* |
| **D** | *l* | *l* | *l* | *l* | *l* | *s* | *l* | *s* | *l* | *l* | *l* | *m* | *l* | *m* | *m* | *s* |
| **E** | *l* | *l* | *l* | *l* | *l* | *m* | *l* | *s* | *l* | *l* | *l* | *s* | *l* | *s* | *m* | *s* |
| none | *l* | *s* | *l* | *s* | *l* | *s* | *l* | *s* | *l* | *s* | *l* | *s* | *l* | *g* | *s* | *s* |

Figure 6
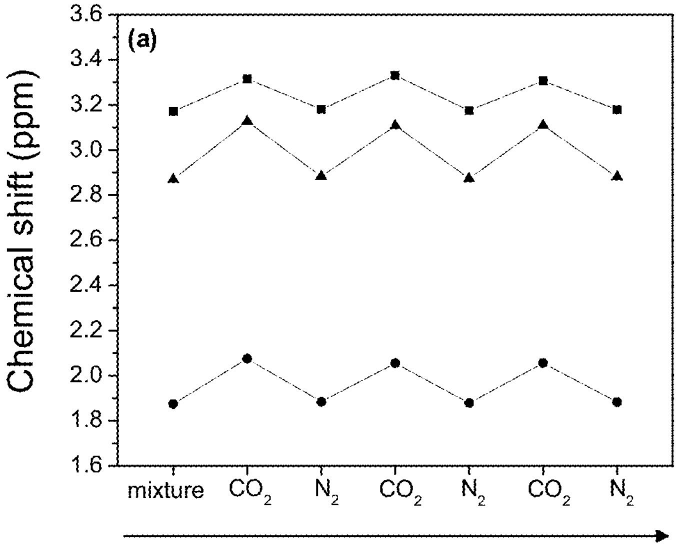
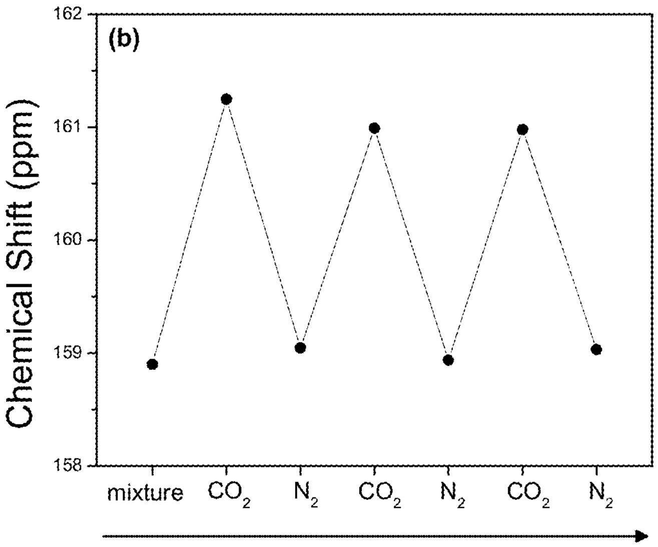

Figure 10

| | Amino alcohol | | | | | | | | | |
|---|---|---|---|---|---|---|---|---|---|---|
| | Prolinol | | Leucinol | | Isoleucinol | | Valinol | | Norephedrine | |
| Amidine | before $CO_2$ | after $CO_2$ | before $CO_2$ | After $CO_2$ | before $CO_2$ | after $CO_2$ | before $CO_2$ | after $CO_2$ | before $CO_2$ | after $CO_2$ |
| $C_4$ | *L* | *L* | *L* | *L* | *L* | *L* | *L* | *L* | *L* | *g* |
| $C_5$ | *L* | *L* | *L* | *M* | *L* | *L* | *L* | *L* | *L* | *g* |
| $C_6$ | *L* | *L* | *L* | *M* | *L* | *L* | *L* | *L* | *L* | *g* |
| $C_7$ | *L* | *L* | *L* | *M* | *L* | *L* | *L* | *L* | *L* | *g* |
| $C_8$ | *L* | *L* | *L* | *M* | *L* | *S* | *L* | *L* | *L* | *g* |
| none | *L* | *L* | *L* | *S* | *S* | *S* | *S* | *S* | *S* | *S* |

Figure 11

| | Amino acid methyl ester | | | | | |
|---|---|---|---|---|---|---|
| | ProMe | | LeuMe | | IleMe | |
| Amidine | before $CO_2$ | after $CO_2$ | before $CO_2$ | After $CO_2$ | before $CO_2$ | after $CO_2$ |
| $C_4$ | | | ***L*** | ***L*** | ***L*** | ***L*** |
| $C_5$ | | | ***L*** | ***L*** | ***L*** | ***L*** |
| $C_6$ | | | ***L*** | ***L*** | ***L*** | ***L*** |
| $C_7$ | | | ***L*** | ***L*** | ***L*** | ***L*** |
| $C_8$ | ***L*** | ***L*** | ***L*** | ***L*** | ***L*** | ***L*** |
| none | ***L*** | ***L*** | ***L*** | ***S*** | ***L*** | ***S*** |

Figure 12

| | Amino acid octyl ester | | | | Amino acid octadecyl ester | | | |
|---|---|---|---|---|---|---|---|---|
| | LeuC8 | | IleC8 | | LeuC18 | | IleC18 | |
| Amidine | before $CO_2$ | after $CO_2$ | before $CO_2$ | After $CO_2$ | before $CO_2$ | after $CO_2$ | before $CO_2$ | after $CO_2$ |
| $C_4$ | ***L*** | ***L*** | ***L*** | ***L*** | ***L*** | ***L***[a] | ***M*** | ***L***[a] |
| $C_5$ | ***L*** | ***L*** | ***L*** | ***L*** | ***L*** | ***L***[a] | ***M*** | ***L***[a] |
| $C_6$ | ***L*** | ***L*** | ***L*** | ***L*** | ***L*** | ***L***[a] | ***M*** | ***L***[a] |
| $C_7$ | ***L*** | ***L*** | ***L*** | ***L*** | ***L*** | ***L***[a] | ***M*** | ***L***[a] |
| $C_8$ | ***L*** | ***L*** | ***L*** | ***L*** | ***L*** | ***L***[a] | ***M*** | ***L***[a] |
| none | ***L*** | ***S*** | ***L*** | ***L*** | ***L*** | ***S*** | ***S*** | ***S*** |

Figure 13

| | 1-Butylamine | | | sec-butylamine | | | t-Butylamine | | |
|---|---|---|---|---|---|---|---|---|---|
| Amidines | before $CS_2$ | after $CS_2$ | after heat | before $CS_2$ | after $CS_2$ | after heat | before $CS_2$ | after $CS_2$ | after heat |
| $C_4$ | | | | | | | | | |
| $C_5$ | | | | | | | | | |
| $C_6$ | **L** | **L** | **L** | **L** | **S** | **S** | **L** | **S** | **S** |
| $C_7$ | | | | | | | | | |
| $C_8$ | | | | | | | | | |
| none | | | | | | | | | |

| | Cyclohexylamine | | | Hexylamine | | | Octylamine | | |
|---|---|---|---|---|---|---|---|---|---|
| Amidines | before $CS_2$ | after $CS_2$ | after heat | before $CS_2$ | after $CS_2$ | after heat | before $CS_2$ | after $CS_2$ | after heat |
| $C_4$ | | | | | | | | | |
| $C_5$ | | | | | | | | | |
| $C_6$ | **L** | **S** | **L** | **L** | **L** | **L** | **L** | **L** | **L** |
| $C_7$ | | | | | | | | | |
| $C_8$ | | | | | | | | | |
| none | | | | | | | | | |

Figure 14

| | | $\alpha_{cell}$ | |
|---|---|---|---|
| **blank (0.2 mm cell)** | 1 | 0.0000 | |
| | 2 | 0.0000 | |
| | 3 | 0.0040 | |
| **Ethanol** | 1 | -0.0005 | -0.0005 |
| | 2 | 0.0000 | 0.0000 |
| | 3 | 0.0045 | 0.0005 |

| **Sample** | **position** | $\alpha°$ | $\alpha° - \alpha_{cell}$ |
|---|---|---|---|
| **1-buthylamine** | 1 | -0.0010 | -0.0010 |
| | 2 | 0.0000 | 0.0000 |
| | 3 | 0.0035 | -0.0005 |
| **C6/1-buthylamine** | 1 | -0.0015 | -0.0015 |
| (before CO2) | 2 | 0.0000 | 0.0000 |
| | 3 | 0.0035 | -0.0005 |
| **C6/1-buthylamine** | 1 | -0.0005 | -0.0005 |
| (after CO2) | 2 | -0.0010 | -0.0010 |
| | 3 | 0.0030 | -0.0010 |
| **sec-buthylamine** | 1 | -0.0015 | -0.0015 |
| | 2 | -0.0015 | -0.0015 |
| | 3 | 0.0035 | -0.0005 |
| **C6/sec-buthylamine** | 1 | -0.0010 | -0.0010 |
| (before CO2) | 2 | -0.0025 | -0.0025 |
| | 3 | 0.0035 | -0.0005 |
| **C6/sec-buthylamine** | 1 | -0.0010 | -0.0010 |
| (after CO2) | 2 | -0.0005 | -0.0005 |
| | 3 | 0.0040 | 0.0000 |
| **LeuMe** | 1 | 0.0185 | 0.0185 |
| | 2 | 0.0180 | 0.0180 |
| | 3 | 0.0220 | 0.0180 |
| **C6/LeuMe** | 1 | 0.0055 | 0.0055 |
| (before CO2 bbl) | 2 | 0.0060 | 0.0060 |
| | 3 | 0.0100 | 0.0060 |
| **C6/LeuMe** | 1 | -0.0210 | -0.0210 |
| (after CO2 bbl) | 2 | -0.0205 | -0.0205 |
| | 3 | -0.0170 | -0.0210 |

L

A

LAC

* = chiral center
L = amidine
A = amino alcohol
LAC = ionic liquid

| L | $R_1$ |
|---|---|
| C4 | n-Butyl |
| C5 | n-Pentyl |
| C6 | n-Hexyl |
| C7 | n-Heptyl |
| C8 | n-Octyl |

A

L-prolinol
L-valinol
L-phenylalaninol
L-methioninol
L-isoleucinol
L-leucinol
(1R,2S)-(-)-norephedrine

| **Sample** | C4-LeuOH-$CO_2$ | C4-IleOH-$CO_2$ | C8-LeuOH-$CO_2$ | C8-IleOH-$CO_2$ |
|---|---|---|---|---|
| **Viscosity (Pa·S)** | 0.28 | 1.51 | 3.78 | 6.50 |

Figure 19

*L-Prolinol/C8 system*

$CO_2$ Uptaken

| Time(min) | 1 | 2 | 3 | 4 | 5 | 6 | 7 | 8 | 9 | 10 |
|---|---|---|---|---|---|---|---|---|---|---|
| % S1 | 15 | 27 | 38 | 49 | 55 | 58 | 61 | 64 | 66 | 67 |
| % S2 | 14 | 24 | 31 | 39 | 46 | 52 | 58 | 61 | 64 | 68 |
| % S3 | 16 | 28 | 38 | 46 | 54 | 58 | 61 | 63 | 65 | 66 |
| % Avg | 15 | 26 | 36 | 45 | 51 | 56 | 60 | 63 | 65 | 67 |
| Time(min) | 15 | 20 | 25 | 30 | 35 | 40 | 45 | 50 | 55 | 60 |
| % S1 | 72 | 75 | 78 | 81 | 84 | 85 | 87 | 88 | 88 | 88 |
| % S2 | 71 | 74 | 77 | 80 | 83 | 86 | 86 | 86 | 86 | 86 |
| % S3 | 69 | 72 | 76 | 79 | 82 | 83 | 85 | 85 | 85 | 85 |
| % Avg | 71 | 74 | 77 | 80 | 83 | 85 | 86 | 87 | 87 | 87 |

*L-Leucinol/C8 system*

$CO_2$ Uptaken

| Time(min) | 1 | 2 | 3 | 4 | 5 | 6 | 7 | 8 | 9 | 10 | | |
|---|---|---|---|---|---|---|---|---|---|---|---|---|
| % S1 | 18 | 31 | 39 | 47 | 55 | 62 | 65 | 68 | 70 | 72 | | |
| % S2 | 18 | 34 | 46 | 52 | 59 | 64 | 67 | 70 | 74 | 77 | | |
| % S3 | 16 | 32 | 42 | 50 | 53 | 58 | 63 | 68 | 71 | 74 | | |
| % Avg | 17 | 33 | 42 | 50 | 56 | 61 | 65 | 69 | 72 | 74 | | |
| Time(min) | 15 | 20 | 25 | 30 | 35 | 40 | 45 | 50 | 55 | 60 | 65 | 70 |
| % S1 | 78 | 85 | 89 | 94 | 99 | 102 | 106 | 107 | 111 | 111 | 111 | 111 |
| % S2 | 84 | 89 | 93 | 97 | 100 | 103 | 105 | 107 | 108 | 108 | 108 | 108 |
| % S3 | 86 | 91 | 94 | 99 | 102 | 105 | 107 | 108 | 110 | 110 | 110 | 110 |
| % Avg | 82 | 88 | 92 | 97 | 100 | 104 | 106 | 107 | 110 | 110 | 110 | 110 |

*L-Valinol/C8 system*

$CO_2$ Uptaken

| Time(min) | 1 | 2 | 3 | 4 | 5 | 6 | 7 | 8 | 9 | 10 | | |
|---|---|---|---|---|---|---|---|---|---|---|---|---|
| % S1 | 10 | 21 | 30 | 38 | 44 | 50 | 57 | 61 | 66 | 70 | | |
| % S2 | 10 | 19 | 28 | 36 | 43 | 51 | 57 | 64 | 70 | 73 | | |
| % S3 | 9 | 19 | 28 | 38 | 47 | 54 | 62 | 67 | 72 | 76 | | |
| % Avg | 10 | 20 | 29 | 37 | 45 | 52 | 59 | 64 | 70 | 73 | | |
| Time(min) | 15 | 20 | 25 | 30 | 35 | 40 | 45 | 50 | 55 | 60 | 65 | 70 |
| % S1 | 75 | 81 | 87 | 92 | 97 | 99 | 102 | 104 | 106 | 107 | 107 | 107 |
| % S2 | 79 | 84 | 88 | 93 | 97 | 102 | 105 | 108 | 111 | 111 | 111 | 111 |
| % S3 | 84 | 89 | 94 | 98 | 102 | 106 | 109 | 111 | 113 | 114 | 114 | 114 |
| % Avg | 80 | 85 | 90 | 95 | 99 | 102 | 105 | 108 | 110 | 111 | 111 | 111 |

Figure 20

| | Amino alcohol | | | | | | | | | | | | | |
|---|---|---|---|---|---|---|---|---|---|---|---|---|---|---|
| | Prolinol | | Leucinol | | Isoleucinol[a] | | Valinol[a] | | Methioninol[a] | | Phenylalaninol[a] | | Norephedrine | |
| Amidine | B | A | B | A | B | A | B | A | B | A | B | A | B | A |
| $C_4$ | **L(L)** | **L(L)** | **L(L)** | **L[b] (L)** | **L(L)** | **L(L)** | **L(L)** | **L(L)** | **L(L)** | **L(L)** | **L(L)** | **L(L)** | **L(L)** | **L(L)** |
| $C_5$ | **L(L)** | **L(L)** | **L(L)** | **L[b](L)** | **L(L)** | **L(L)** | **L(L)** | **L(L)** | **L(L)** | **L(L)** | **L(L)** | **L(L)** | **L(L)** | **L(L)** |
| $C_6$ | **L(L)** | **L(L)** | **L(L)** | **L[b](L)** | **L(L)** | **L(L)** | **L(L)** | **L(L)** | **L(L)** | **L(L)** | **L(L)** | **L(L)** | **L(L)** | **L(L)** |
| $C_7$ | **L(L)** | **L(L)** | **L(L)** | **L[b](L)** | **L(L)** | **L(L)** | **L(L)** | **L(L)** | **L(L)** | **L(L)** | **L(L)** | **L(L)** | **L(L)** | **L(L)** |
| $C_8$ | **L(L)** | **L(L)** | **L(L)** | **L[b](L)** | **L(L)** | **L(L)** | **L(L)** | **L(L)** | **L(L)** | **L(L)** | **L(L)** | **L(L)** | **L(L)** | **L(L)** |
| none | **L** | **L** | **L** | **S** | **S** | **S** | **S** | **S** | **S** | **S** | **S** | **S** | **S** | **S** |

*L, S,* and *G* indicate liquid, solid, and a transparent glass, respectively, at room temperature. [a]Samples were heated slightly above 40 °C until amino alcohols were dissolved before $CO_2$ was bubbled. [b]*M* indicates that the sample was initially a milky-white mixture that became a clear liquid upon further exposure to $CO_2$.

REVERSIBLE ROOM-TEMPERATURE IONIC LIQUIDS

RELATED APPLICATIONS

This application is a continuation of U.S. patent application Ser. No. 12/524,639, filed Dec. 8, 2010, now U.S. Pat. No. 8,574,453, which is a 371 national stage application based on Patent Cooperation Treaty Application serial number PCT/US2008/052161, filed Jan. 28, 2008; which claims the benefit of priority to U.S. Provisional Patent Application Ser. No. 60/898,116, filed Jan. 29, 2007.

GOVERNMENT SUPPORT

This invention was made with support provided by the National Science Foundation (Grant Nos. CHE-0350538 and CHE-0714317); therefore, the government has certain rights in the invention.

BACKGROUND OF THE INVENTION

Ionic liquids are liquids composed of ions that are fluid around or below 100° C. (Rogers, R. D.; Seddon, K. R. *Science* 2003, 302, 792-793). Ionic liquids exhibit negligible vapor pressure, which makes them suitable replacements for conventional solvents. Conventional solvents like dichloromethane, acetone, benzene, and methanol are volatile organic compounds which contaminate soil and groundwater, pollute indoor air, and increase the level of greenhouse gases. Increasing regulatory pressure to limit the use of volatile organic compounds has sparked research into designing ionic liquids that could function as environmentally friendly replacement solvents.

By virtue of their high polarity and charge density, ionic liquids have unique solvating properties, and are being used in a variety of applications. In addition to applications include in organic synthesis as a green solvent, ionic liquid are used in novel materials science (liquid crystals, gels, rubbers); electrochemistry, for example, in fuel cells, electrodeposition processes and other electrochemical applications; in applications where water-based chemistry can be problematic (for example, applications involving proton transfer or nucleophilicity); or in applications where certain coordination chemistry could have a damaging effect on the substrates involved.

Some simple physical properties of the ionic liquids that make them interesting as potential solvents for synthesis are the following: (1) They are good solvents for a wide range of both inorganic and organic materials, and unusual combinations of reagents can be brought into the same phase; (2) They are often composed of poorly coordinating ions, so they have the potential to be highly polar yet noncoordinating solvents; (3) They are immiscible with a number of organic solvents and provide a nonaqueous, polar alternative for two-phase systems; and (4) Ionic liquids are nonvolatile, hence they may be used in high-vacuum systems and eliminate many containment problems (Welton, T. *Chem. Rev.,* 1999, 99, 2071-2083).

A broad range of ionic liquids have been investigated in the past. The most commonly studied systems contain ammonium, phosphonium, pyridinium, or imidazolium cations, with varying heteroatom functionality. Common anions that yield useful ILs include hexafluorophosphate, $[PF_6]^-$; tetrafluoroborate, $[BF_4]^-$; bis(trifyl)imide, $[NTf_2]^-$; and chloride, $Cl^-$. Anions can control the solvent's reactivity with water, coordinating ability, and hydrophobicity.

Accordingly, ionic liquids are relatively advanced, technological solvents that can be designed to fit particular applications (Wasserscheid, P.; Welton, T. *Ionic Liquids in Synthesis*, VCH-Wiley: Weinheim, 2002; Rogers, R. D.; Seddon, K. R., Eds. *Ionic Liquids: Industrial Applications for Green Chemistry*, ACS Symposium Series 818, American Chemical Society: Washington, 2002).

Interest in room-temperature ionic liquids (RTILs) has increased enormously during the last decade because, among other applications, they may be used to replace less environmentally friendly ('green') solvents. Invariably, these ionic liquids are either organic salts or mixtures consisting of at least one organic component. The most common salts in use are those with alkylammonium, alkylphosphonium, N-alkylpyridinium, and N,N'-dialkylimidazolium cations.

A major drawback of many ionic liquids is their air and moisture stability. Many ionic liquids are hygroscopic; if used in open vessels, hydration will almost certainly occur. The degree to which this is a problem will depend on the use to which the ionic liquid is being put and what solutes are being used. For example, the smallest amount of water can deactivate a highly reactive solute used as a catalyst (Chauvin, Y. et al. *Angew. Chem., Int. Ed. Engl.* 1995, 34, 2698-2700).

Similarly, supercritical carbon dioxide has also been employed as a green solvent although it requires specialized equipment and reaction vessels. Carbon dioxide also shows solubility in many ionic liquids. Although it is known that amidines and alcohols react very rapidly with $CO_2$ to form amidinium carbonate salts, some of which are liquids at room temperature, they are stable only under scrupulously dry conditions (Hori, Y. et al., *Chemistry Express* 1986, 1, 224-227). Jessop has demonstrated that the fraction of the amidinium carbonate made by bubbling $CO_2$ through a carefully dried 1/1 mixture of 1,8-diazabicyclo[5.4.0]undec-7-ene (DBU) and 1-hexanol can be returned to its original state by bubbling through $N_2$ or Ar gas (Jessop, P. G. et al., *Nature,* 2005, 436, 1102). However, the uptake of $CO_2$ in DBU/alcohol systems may not be quantitative at 1 atm pressure (Hori, Y. et al., *Chemistry Express* 1986, 1, 173-176). Also, bubbling $CO_2$ through a dilute solution of an N'-alkyl-N,N-dimethylacetamidine in water yields an acyclic amidinium bicarbonate, a reversible surfactant (Liu, Y. et al., *Science* 2006, 313, 958-960).

It is desirable to provide solvent systems whose electrostatic properties can be changed reversibly from relatively low polarity to very high polarity by the addition of different gases. Transparent systems open opportunities for interesting spectroscopic investigations. It is further desirable to develop systems which employ inexpensive precursor amidines and amines, some of which may exhibit liquid crystallinity.

SUMMARY OF THE INVENTION

One aspect of the present invention relates to a class of solvents which can be cycled between a room-temperature ionic liquid (RTIL) state and a non-ionic solvent mixture by exposing the liquids sequentially to a first gas and a second gas. In certain embodiments, the first gas is carbon dioxide. In certain embodiments, the first gas is carbon disulfide. In certain embodiments, the first gas is nitric oxide. In certain embodiments, the first gas is $SO_2$. In certain embodiments, the second gas is an inert gas. In certain embodiments, the inert gas is nitrogen (i.e., dinitrogen).

In certain embodiments, the RTILs of the present invention are derived from the addition of carbon dioxide to a mixture of an aliphatic amidine and an amino acid alcohol. In certain embodiments, the RTILs of the present invention are derived from the addition of carbon dioxide to a mixture of an aliphatic amidine and an amino acid ester. In certain embodiments, the RTILs of the present invention are derived from the addition of carbon disulfide to a mixture of an aliphatic amidine and an amino acid alcohol. In certain embodiments, the RTILs of the present invention are derived from the addition of carbon disulfide to a mixture of an aliphatic amidine and an amino acid ester. In certain embodiments, the aliphatic amidine is optically active. In certain embodiments, the amino acid alcohol is optically active. In certain embodiments, the amino acid ester is optically active. In certain embodiments, the RTILs of the present invention are optically active.

Another aspect of the present invention relates to a class of room-temperature ionic liquids (RTILs) which are derived from a molecule or ion represented by $Y{=}X{=}Z$ or 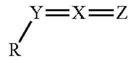

and a mixture of an amidine and an amine. Non-limiting examples of the molecule or ion include: $SO_2$, $NO_2$, $NO_2^-$, $N_3^-$, $SCN^-$, $OCN^-$, R—$N_3$, R—NCO, R—NCS, and R—OCN. These RTILs may be used in any of the methods described herein.

In certain embodiments, the RTILs of the present invention are easily reversible amidinium carbamates derived from the addition of carbon dioxide to a mixture of an aliphatic amidine and an aliphatic primary amine. Remarkably, the ionic liquids of the present invention may be reconverted to low polarity solvents easily and reversibly by reducing the pressure, heating, or bubbling an inert gas through the liquids. In certain embodiments, the inert gas is molecular nitrogen ($N_2$). The useful temperature range may be increased by increasing the pressure of carbon dioxide. Thus, a second liquid component can be expelled or dissolved within the ionic liquid as it is reversed.

In certain embodiments, reversible, optically-active RTILs can be made easily from acyclic amidines and chiral amines. Accordingly, the ionic liquid systems of the invention may be useful in the pharmaceutical industry and other synthetically-related industries. In certain embodiments, these systems may be useful to effect chiral syntheses or separations.

Another aspect of the invention is that these systems obviate the necessity of employing specialized equipment, including maintaining absolutely dry atmospheres, and offer the distinct advantage of creating environments which can be made either to dissolve or phase separate solutes and added liquid components depending on their polarity.

BRIEF DESCRIPTION OF THE FIGURES

FIG. 2 depicts phases of neat 1/1 (mol/mol) amidine/amine mixtures before (B) and after (A) $CO_2$ bubbling. l, s, m, and g indicate (respectively) liquid, solid, liquid-solid mixture, and a glassy transparent material which crystallized partially over a period of weeks.

FIG. 6 depicts the chemical shifts of protons (a) and $^{13}C(N{=}\underline{C}{-}N(CH_3)_2)$ (b) in a 175 mM E+5 in $CDCl_3$ solution upon alternation between $CO_2$ and $N_2$ bubbling. For (a): $N{=}C(\underline{CH_3}){-}N$ (●, 1.85-2.1 ppm), $N{=}C{-}N(\underline{CH_3})_2$ (▲, 2.85-3.15 ppm), and $-\underline{CH_2}N{=}C{-}N$ (■, 3.15-3.35 ppm)

FIG. 10 depicts phases of amidine/amino alcohol mixtures before and after $CO_2$ bubbling. l, s, m, and g indicate (respectively) liquid, solid, liquid-solid mixture, and a glassy transparent material.

FIG. 11 depicts phases of amidine/amino acid methyl ester mixtures before and after $CO_2$ bubbling. l and s indicate (respectively) liquid and solid.

FIG. 12 depicts phases of amidine/amino acid octyl ester and amidine/amino acid octadecyl ester mixtures before and after $CO_2$ bubbling. l, s, m, g, and $l^a$ indicate (respectively) liquid, solid, liquid-solid mixture, glassy transparent material, and a liquid at room temperature which solidified in a refrigerator.

FIG. 13 depicts phases of amidine/amine mixtures before and after $CS_2$ bubbling. l and s indicate (respectively) liquid and solid.

FIG. 14 depicts the optical rotation of chiral solvents which can be or have been cycled between a RTIL state and a non-ionic solvent mixture before and after $CO_2$ bubbling.

FIG. 19 tabulates the time dependence of carbon dioxide uptake at room temperature by various mixtures (1:1 on a molar basis) of amino alcohols and amidines according to the present invention (presented are average values and data for individual samples).

FIG. 20 tabulates the phase appearances of various amino alcohol L/A combinations at room temperature and −20° C. before and after bubbling $CO_2$ through the mixtures.

DETAILED DESCRIPTION OF THE INVENTION

Figure 1:
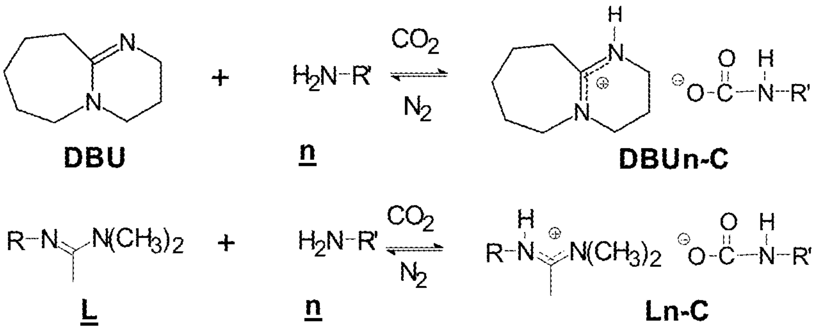
FIG. 1 depicts a class of solvents which can be cycled between a RTIL state and a non-ionic solvent mixture by exposing the liquids sequentially to $CO_2$ and $N_2$.
Figure 3:
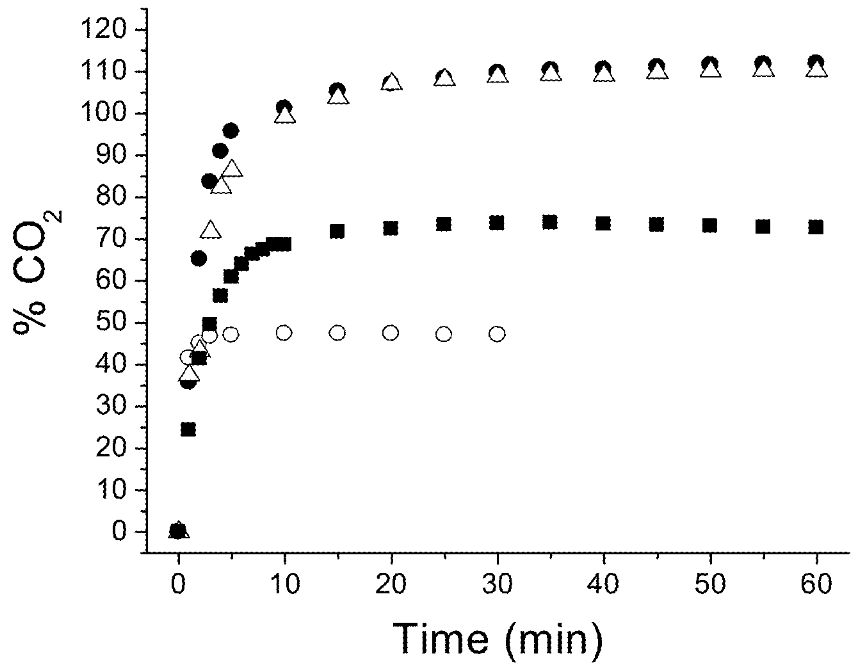
FIG. 3 depicts plots of mole % $CO_2$ uptake by E+5 (●), C+2 (Δ), E+6 (▲), and 5 (○) as a function of time.

One aspect of the present invention relates to a class of solvents which can be cycled between a room-temperature ionic liquid (RTIL) state and a non-ionic solvent mixture by exposing the liquids sequentially to a first gas and a second gas. In certain embodiments, the first gas is carbon dioxide. In certain embodiments, the first gas is carbon disulfide. In certain embodiments, the first gas is nitric oxide. In certain embodiments, the first gas is $SO_2$. In certain embodiments, the second gas is an inert gas. In certain embodiments, the inert gas is molecular nitrogen.

In certain embodiments, the RTILs of the present invention are derived from the addition of carbon dioxide to a mixture of an aliphatic amidine and an amino acid alcohol. In certain embodiments, the RTILs of the present invention are derived from the addition of carbon dioxide to a mixture of an aliphatic amidine and an amino acid ester. In certain embodiments, the RTILs of the present invention are derived from the addition of carbon disulfide to a mixture of an aliphatic amidine and an amino acid alcohol. In certain embodiments, the RTILs of the present invention are derived from the addition of carbon disulfide to a mixture of an aliphatic amidine and an amino acid ester.

In certain embodiments, the aliphatic amidine is optically active. In certain embodiments, the amino acid alcohol is optically active. In certain embodiments, the amino acid ester is optically active. In certain embodiments, the RTILs of the present invention are optically active.

In certain embodiments, the RTILs of the present invention are easily reversible amidinium carbamates derived from the addition of carbon dioxide to a mixture of an aliphatic amidine and an aliphatic primary amine. Remarkably, the ionic liquids of the present invention may be reconverted to low polarity solvents easily and reversibly by reducing the pressure, heating, or bubbling an inert gas through the liquids.

In certain embodiments, the RTILs of the present invention are derived from the addition of carbon dioxide to a mixture of an aliphatic amidine and an amino alcohol. In certain embodiments, the RTILs of the present invention are derived from the addition of carbon dioxide to a mixture of an aliphatic amidine and an amino acid alcohol. In certain embodiments, the RTILs of the present invention are derived from the addition of carbon dioxide to a mixture of an aliphatic amidine and an amino acid ester. In certain embodiments, the RTILs of the present invention are derived from the addition of carbon dioxide to a mixture of an aliphatic amidine and a chiral amino alcohol. In certain embodiments, the RTILs of the present invention are derived from the addition of carbon dioxide to a mixture of an aliphatic amidine and a chiral amino acid alcohol. In certain embodiments, the RTILs of the present invention are derived from the addition of carbon dioxide to a mixture of an aliphatic amidine and a chiral amino acid ester. In certain embodiments, the RTILs of the present invention are derived from the addition of carbon disulfide to a mixture of an aliphatic amidine and an amino alcohol. In certain embodiments, the RTILs of the present invention are derived from the addition of carbon disulfide to a mixture of an aliphatic amidine and an amino acid alcohol. In certain embodiments, the RTILs of the present invention are derived from the addition of carbon disulfide to a mixture of an aliphatic amidine and an amino acid ester. In certain embodiments, the RTILs of the present invention are optically active.

Another aspect of the present invention relates to a class of room-temperature ionic liquids (RTILs) which are derived from a molecule or ion represented by $$Y{=}X{=}Z$$ or 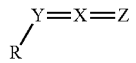

and a mixture of an amidine and an amine. Non-limiting examples of the molecule or ion include: $SO_2$, $NO_2$, $NO_2^-$, $N_3^-$, $SCN^-$, $OCN^-$, R—$N_3$, R—NCO, R—NCS, and R—OCN. These RTILs may be used in any of the methods described herein.

Although it is known that amidines and alcohols react very rapidly with $CO_2$ to form amidinium carbonate salts, some of which are liquids at room temperature, they are stable only under scrupulously dry conditions (Hori, Y. et al., *Chemistry Express* 1986, 1, 224-227). Jessop has demonstrated that the fraction of the amidinium carbonate made by bubbling $CO_2$ through a carefully dried 1/1 mixture of 1,8-diazabicyclo[5.4.0]undec-7-ene (DBU) and 1-hexanol can be returned to its original state by bubbling through $N_2$ or Ar gas (Jessop, P. G. et al., *Nature,* 2005, 436, 1102). However, the uptake of $CO_2$ in DBU/alcohol systems may not be quantitative at 1 atm pressure (Hori, Y. et al., *Chemistry Express* 1986, 1, 173-176). Also, bubbling $CO_2$ through a dilute solution of an N'-alkyl-N,N-dimethylacetamidine in water yields an acyclic amidinium bicarbonate, a reversible surfactant (Liu, Y. et al., *Science* 2006, 313, 958-960).

In certain embodiments where the first gas is carbon dioxide and the second gas is molecular nitrogen, remarkably, the amidine/amine combinations can be interconverted repeatedly at room temperature between their RTIL (Ln-C) and non-ionic liquid forms (L+n) by the treatments shown in FIG. 1.

FIG. 2 depicts phases of neat 1/1 (mol/mol) amidine/amine mixtures before (B) and after (A) $CO_2$ bubbling. Diamines (e.g., 7 and 8) are mixed with 2 molar equivalents of amidines. Amidine/8 mixtures are heated gently to dissolve 8, and then $CO_2$ is bubbled through the warm solutions. When DBU is the amidine, it is dried as described in the literature and distilled (see Jessop, P. G.; Heldebrant, D. J.; Li, X; Eckert, C. A.; Liotta, C. L. *Nature* 2005, 436, 1102).

As shown in FIG. 2, in certain embodiments the phase remains liquid after $CO_2$ bubbling. In other embodiments, a solid, liquid-solid mixture, or a glassy transparent material which crystallizes partially over a period of weeks obtains. Remarkably, 23 can be interconverted repeatedly at room temperature between their RTIL (Ln-C) and non-ionic liquid forms (L+n) by the treatments shown in Scheme 1.

Primary amines react more readily with $CO_2$ than secondary (or tertiary) amines. In certain embodiments, the RTILs are more viscous than the L+n mixtures from which they are made. Qualitatively, the RTILs with 1 and 2 are less viscous than the other Ln-C RTILs made from the same amidine. Evidence for the presence of amidinium carbamates comes from thermal gravimetric analyses (TGA) of the weight loss of $CO_2$ upon heating, from following the quantitative uptake of $CO_2$ by the L+n mixtures as a function of time, and from comparisons of IR spectra of the amidine/amine mixtures before and after addition of $CO_2$. In certain embodiments, the uptake of $CO_2$ by neat amidine/amine solutions (including those with DBU as the amidine) is quantitative within experimental error when the resulting amidinium carbamate is a liquid at room temperature (as opposed to neat DBU/alkanol toluene solutions).

In certain embodiments, in the absence of $CO_2$ the amidine/amine combinations yield liquids at room temperature. In an embodiment with 1,6-dimethylaminohexane (8), yielded a room temperature liquid solution is made by heating it gently in the presence of an amidine partner. In certain embodiments, the combinations employing 'dried' DBU remain liquids after addition of $CO_2$ except those with 8 or the bulkiest amine, t-butylamine (3).

The sensitivity of the systems to moisture depends on the nature of the primary amine. When commercial DBU is used as received, only n-butyl amine (1) and 1,2-diaminoethylene (7) yield RTILs upon addition of $CO_2$. Some RTILs employing even "dried" DBU (DBU1-C, DBU2-C, DBU5-C, and DBU6-C) become cloudy after standing for one day, indicating the aggregation of amidinium bicarbonates from residual water. However, when $CO_2$ is bubbled through C+1 containing 3 wt % of added water, a liquid phase obtains and persists for long periods. Quite remarkably, the aliphatic amidine/amine systems can be easily adapted for many applications without maintaining scrupulously dry conditions.

In certain embodiments, longer chain lengths may discourage RTIL formation. A comparison of the results from the acyclic amidines with the isomeric butyl amines (1-3) provides additional insights into the dependence of the phase formed upon $CO_2$ bubbling and the molecular structures of the constituent molecules. The unbranched n-butyl and sec-butyl amines yield ionic liquids with all of the acyclic amidines studied; however, t-butyl amine produces only solids. In other embodiments, the acyclic amidines with the shortest n-alkyl chain lengths yield RTILs with cyclohexyl amine (4) and n-octyl amine (6).

Another aspect of the present invention is the quantitative uptake of $CO_2$. The time dependence of the uptake of $CO_2$ by stirred mixtures of C+2, E+5, and E+6, as well as by neat 5, can be followed using a gas burette filled with one atmosphere pressure of $CO_2$. In certain embodiments, about one-half an equivalent of $CO_2$ (47%) is taken up by neat 5; the formation of hexylammonium N-hexylcarbamate is virtually quantitative. Although the time profiles for uptake of the $CO_2$ gas must depend to some extent on the rate of stirring and the liquid-gas surface area, the data shows that the two mixtures which form RTILs (C+2 and E+5) behave very differently from the mixture which leads to a solid, E+6. In certain embodiments, uptake of $CO_2$ by C+2 and E+5 is rapid initially and then continues very slowly, reaching a plateau value after ca. 30 min. The eventual uptake exceeds the theoretical amount by ca. 4 and 10%, respectively. The solubility of $CO_2$ gas in many ILs is known to be very high. Both the excess amount and the time profile for its uptake indicate that the rapid (ca. 100%) part is due to formation of the RTIL; thereafter, more $CO_2$ dissolves in the ionic phase. In other embodiments the rate of uptake by E+6, leading to E6-C, is initially as rapid as with the other amidine/amine samples, but slows after a short period of time and reaches an eventual plateau corresponding to only ca. 73% of the theoretical value because solidification of E6-C traps the remaining liquid of E+6 and isolates it from contact with $CO_2$.

Another aspect of the present invention is the ability of these systems to dissolve reversibly dissolve less polar materials into the L+n and separate them from Ln-C as it is formed. For example, after bubbling $CO_2$ through a transparent solution of E+5 and n-decane for <1 min, the solution becomes opaque, but remains liquid. After additional bubbling for 30 min and then standing for 60 min or centrifuging for a short period, the sample separates into two liquid phases. In fact, phase separation can be achieved after as little as 1 min of $CO_2$ bubbling followed by standing. In other embodiments, cycling between one and two liquid phases can be repeated 3 times by bubbling $CO_2$ and $N_2$ sequentially to demonstrate the reversibility of the process. Remarkably, several interesting applications can be envisioned for solvent systems whose electrostatic properties can be changed reversibly from relatively low polarity to very high polarity by the addition of different gases. Additionally, the virtual transparency of both the L+n and Ln-C above ca. 350 nm and very low absorption at 300-350 nm opens opportunities for interesting spectroscopic investigations. The low cost of and easy access to the precursor amidines and amines add to the attractive features of these systems.

DEFINITIONS

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The terms "amine" and "amino" are art-recognized and refer to both unsubstituted and substituted amines, e.g., a moiety that may be represented by the general formulas:

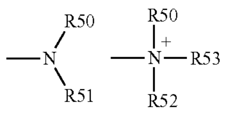

wherein R50, R51 and R52 each independently represent a hydrogen, an alkyl, an alkenyl, $-(CH_2)_m-$R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or $-(CH_2)_m-$R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

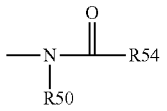

wherein R50 is as defined above, and R54 represents a hydrogen, an alkyl, an alkenyl or $-(CH_2)_m-$R61, where m and R61 are as defined above.

The term "amido" is art recognized as an amino-substituted carbonyl and includes a moiety that may be represented by the general formula:

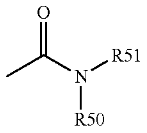

wherein R50 and R51 are as defined above. Certain embodiments of the amide in the present invention will not include imides which may be unstable.

The term "amidine" refers to moieties that can be represented by the formula:

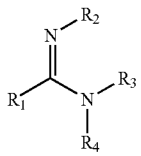

wherein $R_1$, $R_2$, $R_3$, and $R_4$ each independently is a hydrocarbon moiety comprised of carbon chains or rings of up to 26 carbon atoms to which hydrogen atoms are attached. The term includes alkyl, cycloalkyl, alkenyl, alkynyl, and aryl groups, groups which have a mixture of saturated and unsaturated bonds, carbocyclic rings, and includes combinations of such groups. In certain embodiments $R_1$ and $R_4$, $R_2$ and $R_3$, or both ($R_1$ and $R_4$) and ($R_2$ and $R_3$) taken together with the N atom to which they are attached complete a heterocycle having from 4 to 8 atoms in the ring structure.

The term "amidinium" refers to moieties that can be represented by the formula:

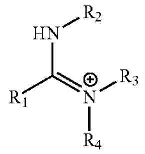

wherein $R_1$, $R_2$, $R_3$, and $R_4$ each independently is a hydrocarbon moiety comprised of carbon chains or rings of up to 26 carbon atoms to which hydrogen atoms are attached. The term includes alkyl, cycloalkyl, alkenyl, alkynyl, and aryl groups, groups which have a mixture of saturated and unsaturated bonds, carbocyclic rings, and includes combinations of such groups. In certain embodiments $R_1$ and $R_4$, $R_2$ and $R_3$, or both ($R_1$ and $R_4$) and ($R_2$ and $R_3$) taken together with the N atom to which they are attached complete a heterocycle having from 4 to 8 atoms in the ring structure.

The term "carboxyl" is art recognized and includes such moieties as may be represented by the general formulas:

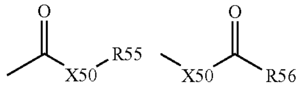

wherein X50 is a bond or represents an oxygen or a sulfur, and R55 and R56 represents a hydrogen, an alkyl, an alkenyl, $-(CH_2)_m-$R61 or a pharmaceutically acceptable salt, R56 represents a hydrogen, an alkyl, an alkenyl or $-(CH_2)_m-$R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamate" refers to moieties as can be represented by the formula:

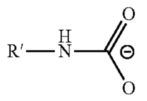

wherein R' is a hydrocarbon moiety comprised of carbon chains or rings of up to 26 carbon atoms to which hydrogen atoms are attached. The term includes alkyl, cycloalkyl, alkenyl, alkynyl, and aryl groups, groups which have a mixture of saturated and unsaturated bonds, carbocyclic rings, and includes combinations of such groups. It may refer to straight chain, branched-chain, cyclic structures, or combinations thereof.

The term “dithiocarbamate” refers to moieties as can be represented by the formula:

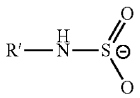

wherein R' is a hydrocarbon moiety comprised of carbon chains or rings of up to 26 carbon atoms to which hydrogen atoms are attached. The term includes alkyl, cycloalkyl, alkenyl, alkynyl, and aryl groups, groups which have a mixture of saturated and unsaturated bonds, carbocyclic rings, and includes combinations of such groups. It may refer to straight chain, branched-chain, cyclic structures, or combinations thereof.

The definition of each expression, e.g. alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations.*

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that “substitution” or “substituted with” includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term “substituted” is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics,* 67th Ed., 1986-87, inside cover.

Compounds of the Invention

In certain embodiments, the invention relates to a salt represented by:

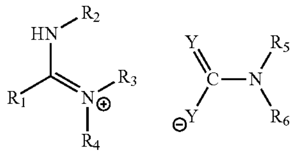

wherein $R_1$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, or $-C(R_8)_3$;

$R_2$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, or $-C(R_8)_3$;

$R_3$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, or $-C(R_8)_3$;

$R_4$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, or $-C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, $-C(R_8)_3$, or $-(CH_2)_n-NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, $-C(R_8)_3$, or $-(CH_2)_n-NH_2$;

Y represents independently for each occurrence O or S;

$R_8$ represents independently for each occurrence $-(CH_2)_n-CH_3$, cycloalkyl, aryl, or heteroaryl; and n represents independently for each occurrence an integer in the range 1-10 inclusive.

In certain embodiments, the invention relates to the aforementioned salt, wherein $R_1$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$;

$R_2$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$;

$R_3$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$;

$R_4$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$.

In certain embodiments, the invention relates to the aforementioned salt, wherein $R_1$ represents H, alkyl, fluoroalkyl, cycloalkyl, heterocycloalkyl, $-(CH_2)_n-R_8$, $-CH(R_8)_2$, or $-C(R_8)_3$;

$R_2$ represents H, alkyl, fluoroalkyl, cycloalkyl, heterocycloalkyl, $-(CH_2)_n-R_8$, $-CH(R_8)_2$, or $-C(R_8)_3$;

$R_3$ represents H, alkyl, fluoroalkyl, cycloalkyl, heterocycloalkyl, $-(CH_2)_n-R_8$, $-CH(R_8)_2$, or $-C(R_8)_3$;

$R_4$ represents H, alkyl, fluoroalkyl, cycloalkyl, heterocycloalkyl, $-(CH_2)_n-R_8$, $-CH(R_8)_2$, or $-C(R_8)_3$;

$R_5$ represents H, alkyl, fluoroalkyl, cycloalkyl, heterocycloalkyl, $-(CH_2)_n-R_8$, $-CH(R_8)_2$, or $-C(R_8)_3$; and $R_6$ represents H, alkyl, fluoroalkyl, cycloalkyl, heterocycloalkyl, $-(CH_2)_n-R_8$, $-CH(R_8)_2$, or $-C(R_8)_3$.

In certain embodiments, the invention relates to the aforementioned salt, wherein $R_1$ represents H, alkyl, fluoroalkyl, cycloalkyl, heterocycloalkyl, $-(CH_2)_n-R_8$, $-CH(R_8)_2$, or $-C(R_8)_3$;

$R_2$ represents H, alkyl, fluoroalkyl, cycloalkyl, heterocycloalkyl, $-(CH_2)_n-R_8$, $-CH(R_8)_2$, or $-C(R_8)_3$;

$R_3$ represents H, alkyl, fluoroalkyl, cycloalkyl, heterocycloalkyl, $-(CH_2)_n-R_8$, $-CH(R_8)_2$, or $-C(R_8)_3$;

$R_4$ represents H, alkyl, fluoroalkyl, cycloalkyl, heterocycloalkyl, $-(CH_2)_n-R_8$, $-CH(R_8)_2$, or $-C(R_8)_3$;

$R_5$ represents H, alkyl, fluoroalkyl, cycloalkyl, heterocycloalkyl, $-(CH_2)_n-R_8$, $-CH(R_8)_2$, or $-C(R_8)_3$;

$R_6$ represents H, alkyl, fluoroalkyl, cycloalkyl, heterocycloalkyl, $-(CH_2)_n-R_8$, $-CH(R_8)_2$, or $-C(R_8)_3$; and Y is O.

In certain embodiments, the invention relates to the aforementioned salt, wherein Y is O.

In certain embodiments, the invention relates to the aforementioned salt, wherein Y is O; and $R_1$, $R_3$, and $R_4$ are methyl.

In certain embodiments, the invention relates to the aforementioned salt, wherein Y is O;

$R_1$, $R_3$, and $R_4$ are methyl; and $R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned salt, wherein Y is O;

$R_1$, $R_3$, and $R_4$ are methyl; and $R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned salt, wherein Y is O;

$R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$; and $R_5$ is H.

In certain embodiments, the invention relates to the aforementioned salt, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

Y is O;

$R_5$ is H; and $R_6$ represents n-$C_4H_9$, sec-$C_4H_9$, t-$C_4H_9$, cyclohexyl, n-$C_6H_{13}$, n-$C_8H_{17}$, $-C_2H_4NH_2$, or $-C_6H_{12}NH_2$.

In certain embodiments, the invention relates to the aforementioned salt, wherein $R_1$, $R_3$, and $R_4$ are methyl;

$R_2$ is n-$C_8H_{17}$;

Y is O;

$R_5$ is H; and $R_6$ represents n-$C_4H_9$ or n-$C_8H_{17}$.

In certain embodiments, the invention relates to the aforementioned salt, wherein $R_1$ represents H, alkyl, fluoroalkyl, cycloalkyl, heterocycloalkyl, $-(CH_2)_n-R_8$, $-CH(R_8)_2$, or $-C(R_8)_3$;

$R_2$ represents H, alkyl, fluoroalkyl, cycloalkyl, heterocycloalkyl, $-(CH_2)_n-R_8$, $-CH(R_8)_2$, or $-C(R_8)_3$;

$R_3$ represents H, alkyl, fluoroalkyl, cycloalkyl, heterocycloalkyl, $-(CH_2)_n-R_8$, $-CH(R_8)_2$, or $-C(R_8)_3$;

$R_4$ represents H, alkyl, fluoroalkyl, cycloalkyl, heterocycloalkyl, $-(CH_2)_n-R_8$, $-CH(R_8)_2$, or $-C(R_8)_3$;

$R_5$ represents H, alkyl, fluoroalkyl, cycloalkyl, heterocycloalkyl, $-(CH_2)_n-R_8$, $-CH(R_8)_2$, or $-C(R_8)_3$;

$R_6$ represents H, alkyl, fluoroalkyl, cycloalkyl, heterocycloalkyl, $-(CH_2)_n-R_8$, $-CH(R_8)_2$, or $-C(R_8)_3$; and Y is S.

In certain embodiments, the invention relates to the aforementioned salt, wherein Y is S.

In certain embodiments, the invention relates to the aforementioned salt, wherein Y is O; and $R_1$, $R_3$, and $R_4$ are methyl.

In certain embodiments, the invention relates to the aforementioned salt, wherein Y is S;

$R_1$, $R_3$, and $R_4$ are methyl; and $R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned salt, wherein Y is S;

$R_1$, $R_3$, and $R_4$ are methyl; and $R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned salt, wherein Y is S;

$R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$; and $R_5$ is H.

In certain embodiments, the invention relates to the aforementioned salt, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

Y is S;

$R_5$ is H; and $R_6$ represents n-$C_4H_9$, sec-$C_4H_9$, t-$C_4H_9$, cyclohexyl, n-$C_6H_{13}$, n-$C_8H_{17}$, $-C_2H_4NH_2$, or $-C_6H_{12}NH_2$.

In certain embodiments, the invention relates to the aforementioned salt, wherein $R_1$, $R_3$, and $R_4$ are methyl;

$R_2$ is n-$C_8H_{17}$;

Y is S;

$R_5$ is H; and $R_6$ represents n-$C_4H_9$ or n-$C_8H_{17}$.

In certain embodiments, the invention relates to the aforementioned salt, wherein said salt is represented by

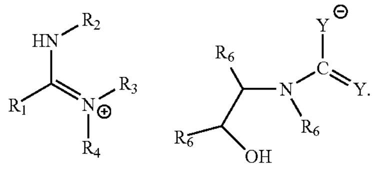

In certain embodiments, the invention relates to the aforementioned salt, wherein said salt is represented by

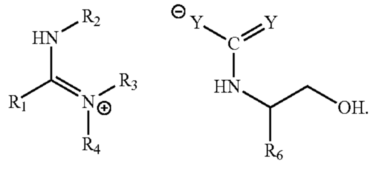

In certain embodiments, the invention relates to the aforementioned salt, wherein said salt is represented by

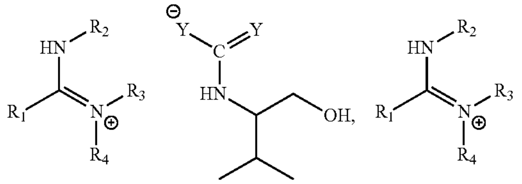

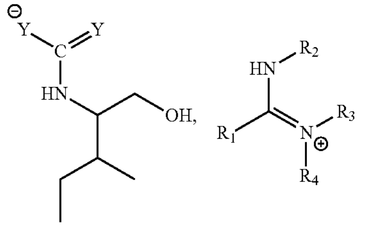

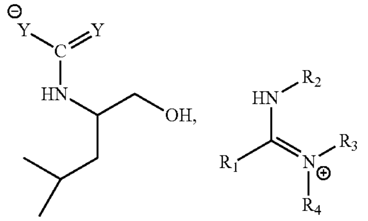

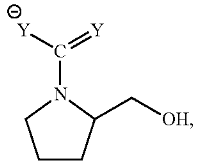

or

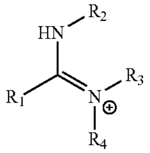

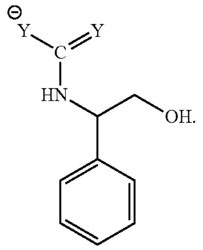

In certain embodiments, the invention relates to the aforementioned salt, wherein said salt is represented by

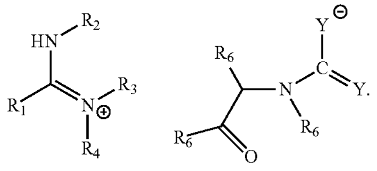

In certain embodiments, the invention relates to the aforementioned salt, wherein said salt is represented by

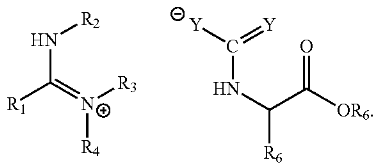

In certain embodiments, the invention relates to the aforementioned salt, wherein said salt is represented by

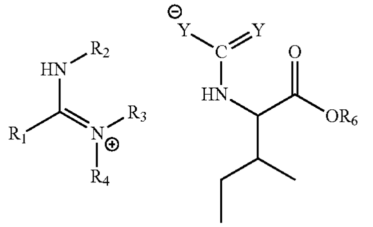

or

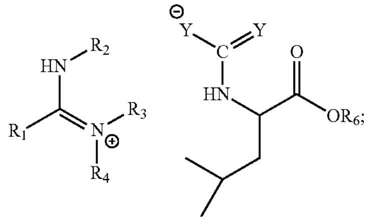

wherein $R_6$ is represented by n-$C_8H_{17}$ or n-$C_{18}H_{37}$.

In certain embodiments, the invention relates to the aforementioned salt, wherein said salt is represented by

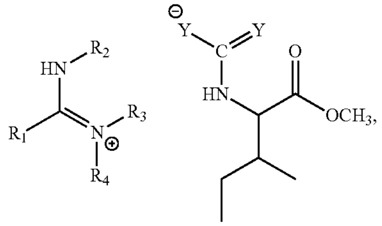

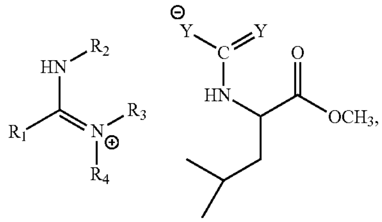

or

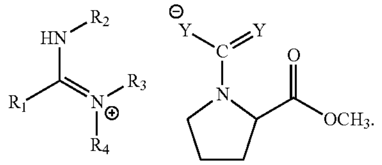

In certain embodiments, the invention relates to a salt represented by

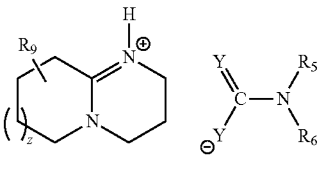

wherein $R_9$ is absent or represents one or more substituents attached to the ring, each of which is independently selected from the group consisting of H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, $—C(R_8)_3$, and $—(CH_2)_n—NH_2$;

z is zero or an integer in the range of 1 to 3;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, $—C(R_8)_3$, or $—(CH_2)_n—NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, $—C(R_8)_3$, or $—(CH_2)_n—NH_2$;

Y represents independently for each occurrence O or S;

$R_8$ represents independently for each occurrence $—(CH_2)_n—CH_3$, cycloalkyl, aryl, or heteroaryl; and n represents independently for each occurrence an integer in the range 1-10 inclusive.

In certain embodiments, the invention relates to the aforementioned salt, wherein $R_9$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$.

In certain embodiments, the invention relates to the aforementioned salt, wherein $R_9$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$; and $R_6$ represents H, alkyl, fluoroalkyl, cycloalkyl, heterocycloalkyl, $—(CH_2)_n—R_8$, $—CH(R_8)_2$, or $—C(R_8)_3$.

In certain embodiments, the invention relates to the aforementioned salt, wherein $R_9$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$;

$R_6$ represents H, alkyl, fluoroalkyl, cycloalkyl, heterocycloalkyl, $—(CH_2)_n—R_8$, $—CH(R_8)_2$, or $—C(R_8)_3$; and Y is O.

In certain embodiments, the invention relates to the aforementioned salt, wherein Y is O.

In certain embodiments, the invention relates to the aforementioned salt, wherein Y is O; and $R_9$ is absent.

In certain embodiments, the invention relates to the aforementioned salt, wherein Y is O;

$R_9$ is absent; and z is 0 or 1.

In certain embodiments, the invention relates to the aforementioned salt, wherein Y is O;

$R_9$ is absent;

z is 0 or 1; and $R_5$ is H.

In certain embodiments, the invention relates to the aforementioned salt, wherein Y is O;

$R_9$ is absent;

z is 0 or 1;

$R_5$ is H; and $R_6$ represents n-$C_4H_9$, sec-$C_4H_9$, t-$C_4H_9$, cyclohexyl, n-$C_6H_{13}$, n-$C_8H_{17}$, $-C_2H_4NH_2$, or $-C_6H_{12}NH_2$.

In certain embodiments, the invention relates to the aforementioned salt, wherein Y is O;

$R_9$ is absent;

z is 0 or 1;

$R_5$ is H; and $R_6$ represents n-$C_4H_9$ or $-C_2H_4NH_2$.

In certain embodiments, the invention relates to the aforementioned salt, wherein $R_9$ represents H, alkyl, fluoroalkyl, cycloalkyl, heterocycloalkyl, $-(CH_2)_n-R_8$, $-CH(R_8)_2$, or $-C(R_8)_3$;

$R_5$ represents H, alkyl, fluoroalkyl, cycloalkyl, heterocycloalkyl, $-(CH_2)_n-R_8$, $-CH(R_8)_2$, or $-C(R_8)_3$;

$R_6$ represents H, alkyl, fluoroalkyl, cycloalkyl, heterocycloalkyl, $-(CH_2)_n-R_8$, $-CH(R_8)_2$, or $-C(R_8)_3$; and Y is S.

In certain embodiments, the invention relates to the aforementioned salt, wherein Y is S.

In certain embodiments, the invention relates to the aforementioned salt, wherein Y is S; and $R_9$ is absent.

In certain embodiments, the invention relates to the aforementioned salt, wherein Y is S;

$R_9$ is absent; and z is 0 or 1.

In certain embodiments, the invention relates to the aforementioned salt, wherein Y is S;

$R_9$ is absent;

z is 0 or 1; and $R_5$ is H.

In certain embodiments, the invention relates to the aforementioned salt, wherein Y is S;

$R_9$ is absent;

z is 0 or 1;

$R_5$ is H; and $R_6$ represents n-$C_4H_9$, sec-$C_4H_9$, t-$C_4H_9$, cyclohexyl, n-$C_6H_{13}$, n-$C_8H_{17}$, $-C_2H_4NH_2$, or $-C_6H_{12}NH_2$.

In certain embodiments, the invention relates to the aforementioned salt, wherein Y is S;

$R_9$ is absent;

z is 0 or 1;

$R_5$ is H; and $R_6$ represents n-$C_4H_9$ or $-C_2H_4NH_2$.

In certain embodiments, the invention relates to the aforementioned salt, wherein said salt is represented by

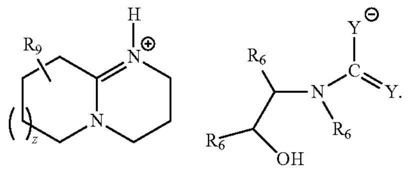

In certain embodiments, the invention relates to the aforementioned salt, wherein said salt is represented by

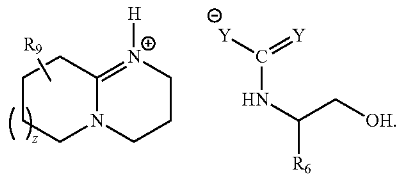

In certain embodiments, the invention relates to the aforementioned salt, wherein said salt is represented by

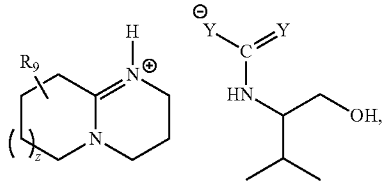

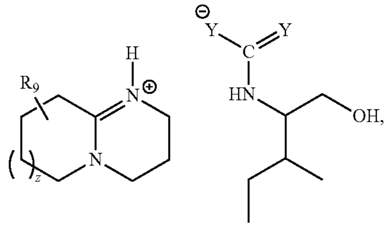

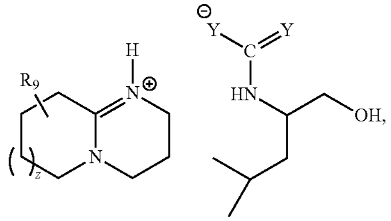

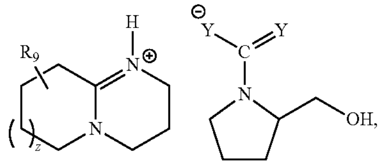

or

-continued

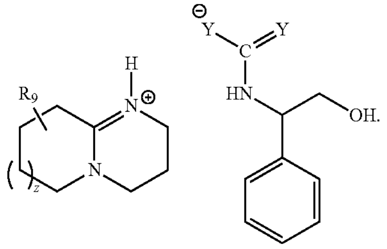

In certain embodiments, the invention relates to the aforementioned salt, wherein said salt is represented by

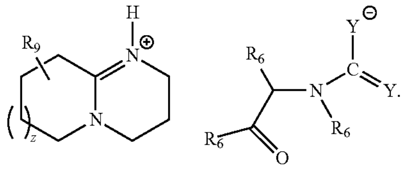

In certain embodiments, the invention relates to the aforementioned salt, wherein said salt is represented by

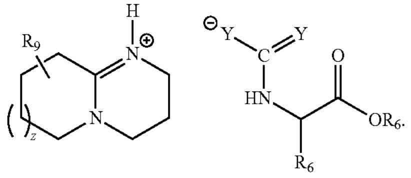

In certain embodiments, the invention relates to the aforementioned salt, wherein said salt is represented by

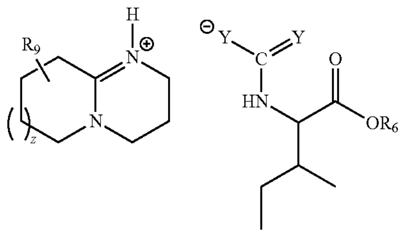

or

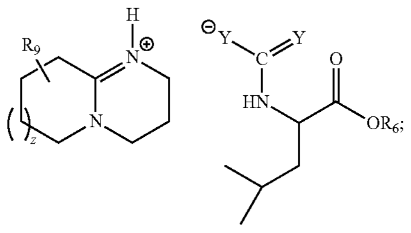

wherein $R_6$ is represented by n-$C_8H_{17}$ or n-$C_{18}H_{37}$.

In certain embodiments, the invention relates to the aforementioned salt, wherein said salt is represented by

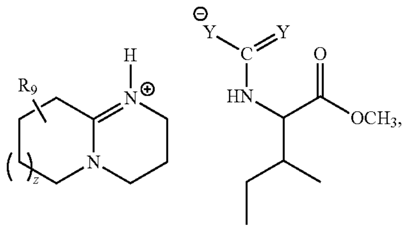

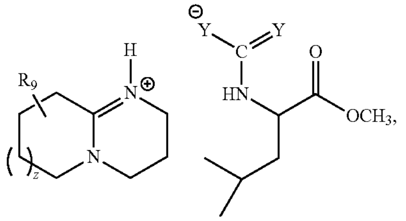

or

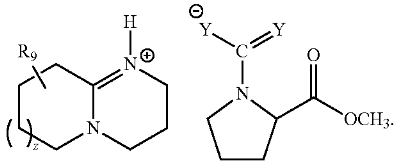

In certain embodiments, the invention relates to a salt represented by:

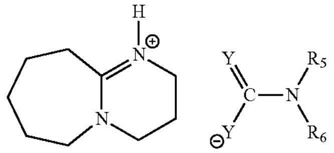

wherein $R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, $-C(R_8)_3$, or $-(CH_2)_n-NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, $-C(R_8)_3$, or $-(CH_2)_n-NH_2$;

Y represents independently for each occurrence O or S;

$R_8$ represents independently for each occurrence $-(CH_2)_n-CH_3$, cycloalkyl, aryl, or heteroaryl; and n represents independently for each occurrence an integer in the range 1-10 inclusive.

In certain embodiments, the invention relates to the aforementioned salt, wherein $R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$.

In certain embodiments, the invention relates to the aforementioned salt, wherein $R_5$ represents H, alkyl, fluoroalkyl, cycloalkyl, heterocycloalkyl, $-(CH_2)_n-R_8$, $-CH(R_8)_2$, or $-C(R_8)_3$; and $R_6$ represents H, alkyl, fluoroalkyl, cycloalkyl, heterocycloalkyl, $-(CH_2)_n-R_8$, $-CH(R_8)_2$, or $-C(R_8)_3$.

In certain embodiments, the invention relates to the aforementioned salt, wherein $R_5$ represents H, alkyl, fluoroalkyl, cycloalkyl, heterocycloalkyl, $-(CH_2)_n-R_8$, $-CH(R_8)_2$, or $-C(R_8)_3$;

$R_6$ represents H, alkyl, fluoroalkyl, cycloalkyl, heterocycloalkyl, $-(CH_2)_n-R_8$, $-CH(R_8)_2$, or $-C(R_8)_3$; and Y is O.

In certain embodiments, the invention relates to the aforementioned salt, wherein Y is O.

In certain embodiments, the invention relates to the aforementioned salt, wherein Y is O; and $R_5$ is H.

In certain embodiments, the invention relates to the aforementioned salt, wherein Y is O;

$R_5$ is H; and $R_6$ represents n-$C_4H_9$, sec-$C_4H_9$, t-$C_4H_9$, cyclohexyl, n-$C_6H_{13}$, n-$C_8H_{17}$, $-C_2H_4NH_2$, or $-C_6H_{12}NH_2$.

In certain embodiments, the invention relates to the aforementioned salt, wherein Y is O;

$R_5$ is H; and $R_6$ represents n-$C_4H_9$ or $-C_2H_4NH_2$.

In certain embodiments, the invention relates to the aforementioned salt, wherein $R_5$ represents H, alkyl, fluoroalkyl, cycloalkyl, heterocycloalkyl, $-(CH_2)_n-R_8$, $-CH(R_8)_2$, or $-C(R_8)_3$;

$R_6$ represents H, alkyl, fluoroalkyl, cycloalkyl, heterocycloalkyl, $-(CH_2)_n-R_8$, $-CH(R_8)_2$, or $-C(R_8)_3$; and Y is S.

In certain embodiments, the invention relates to the aforementioned salt, wherein Y is S.

In certain embodiments, the invention relates to the aforementioned salt, wherein Y is S; and $R_5$ is H.

In certain embodiments, the invention relates to the aforementioned salt, wherein Y is S;

$R_5$ is H; and $R_6$ represents n-$C_4H_9$, sec-$C_4H_9$, t-$C_4H_9$, cyclohexyl, n-$C_6H_{13}$, n-$C_8H_{17}$, $-C_2H_4NH_2$, or $-C_6H_{12}NH_2$.

In certain embodiments, the invention relates to the aforementioned salt, wherein Y is S;

$R_5$ is H; and $R_6$ represents n-$C_4H_9$ or $-C_2H_4NH_2$.

Methods of the Invention

In certain embodiments, the invention relates to a method of preparing a salt, comprising the step of contacting a gas with a first compound and a second compound, wherein said first compound is selected from the group consisting of

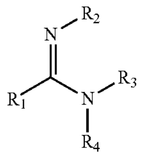

and

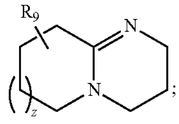

;

wherein $R_1$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, or $-C(R_8)_3$;

$R_2$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, or $-C(R_8)_3$;

$R_3$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, or $-C(R_8)_3$;

$R_4$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, or $-C(R_8)_3$;

$R_8$ represents independently for each occurrence $-(CH_2)_n-CH_3$, cycloalkyl, aryl, or heteroaryl; and n represents independently for each occurrence an integer in the range 1-10 inclusive;

$R_9$ is absent or represents one or more substituents attached to the ring, each of which is independently selected from the group consisting of H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, $-C(R_8)_3$, and $-(CH_2)_n-NH_2$;

z is zero or an integer in the range of 1 to 3; and said second compound is represented by

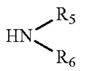

wherein $R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, $—C(R_8)_3$, or $—(CH_2)_n—NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, $—C(R_8)_3$, or $—(CH_2)_n—NH_2$;

$R_8$ represents independently for each occurrence $—(CH_2)_n—CH_3$, cycloalkyl, aryl, or heteroaryl;

n represents independently for each occurrence an integer in the range 1-10 inclusive; and said gas is represented by:

$$Y=X=Y$$

wherein

X represents C or N; and

Y represents independently for each occurrence O or S.

In certain embodiments, the invention relates to the aforementioned method, wherein $R_1$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$;

$R_2$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$;

$R_3$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$;

$R_4$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, or $—CH(R_8)_2$, or $—C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$.

In certain embodiments, the invention relates to the aforementioned method, wherein $R_1$ represents H, alkyl, fluoroalkyl, cycloalkyl, heterocycloalkyl, $—(CH_2)_n—R_8$, $—CH(R_8)_2$, or $—C(R_8)_3$;

$R_2$ represents H, alkyl, fluoroalkyl, cycloalkyl, heterocycloalkyl, $—(CH_2)_n—R_8$, $—CH(R_8)_2$, or $—C(R_8)_3$;

$R_3$ represents H, alkyl, fluoroalkyl, cycloalkyl, heterocycloalkyl, $—(CH_2)_n—R_8$, $—CH(R_8)_2$, or $—C(R_8)_3$;

$R_4$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$; and $R_6$ represents H, alkyl, fluoroalkyl, cycloalkyl, heterocycloalkyl, $—(CH_2)_n—R_8$, $—CH(R_8)_2$, or $—C(R_8)_3$.

In certain embodiments, the invention relates to the aforementioned method, wherein $R_1$ represents H, alkyl, fluoroalkyl, cycloalkyl, heterocycloalkyl, $—(CH_2)_n—R_8$, $—CH(R_8)_2$, or $—C(R_8)_3$;

$R_2$ represents H, alkyl, fluoroalkyl, cycloalkyl, heterocycloalkyl, $—(CH_2)_n—R_8$, $—CH(R_8)_2$, or $—C(R_8)_3$;

$R_3$ represents H, alkyl, fluoroalkyl, cycloalkyl, heterocycloalkyl, $—(CH_2)_n—R_8$, $—CH(R_8)_2$, or $—C(R_8)_3$;

$R_4$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$;

$R_6$ represents H, alkyl, fluoroalkyl, cycloalkyl, heterocycloalkyl, $—(CH_2)_n—R_8$, $—CH(R_8)_2$, or $—C(R_8)_3$; and Y is O.

In certain embodiments, the invention relates to the aforementioned method, wherein said second compound is represented by

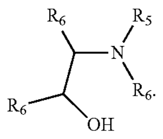

In certain embodiments, the invention relates to the aforementioned method, wherein said second compound is represented by

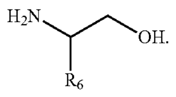

In certain embodiments, the invention relates to the aforementioned method, wherein said second compound is selected from the group consisting of prolinol, leucinol, isoleucinol, valinol, and norephedrine.

In certain embodiments, the invention relates to the aforementioned method, wherein said second compound is represented by

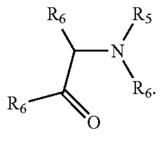

In certain embodiments, the invention relates to the aforementioned method, wherein said second compound is represented by

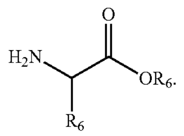

In certain embodiments, the invention relates to the aforementioned method, wherein said second compound is selected from the group consisting of leucine octyl ester, isoleucine octyl ester, leucine octadecyl ester, and isoleucine octadecyl ester.

In certain embodiments, the invention relates to the aforementioned method, wherein said second compound is selected from the group consisting of leucine proline methyl ester, leucine methyl ester, and isoleucine methyl ester.

In certain embodiments, the invention relates to the aforementioned method, wherein X is C;

Y is S;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is S;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein X is C; and Y is O.

In certain embodiments, the invention relates to the aforementioned method, wherein X is C;

Y is O; and $R_1$, $R_3$, and $R_4$ are methyl.

In certain embodiments, the invention relates to the aforementioned method, wherein X is C;

Y is O;

$R_1$, $R_3$, and $R_4$ are methyl; and $R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned method, wherein X is C;

Y is O;

$R_1$, $R_3$, and $R_4$ are methyl; and $R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned method, wherein X is C;

Y is O;

$R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$; and $R_5$ is H.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein $R_1$, $R_3$, and $R_4$ are methyl;

$R_2$ is n-$C_8H_{17}$;

X is C;

Y is O;

$R_5$ is H; and $R_6$ represents n-$C_4H_9$ or n-$C_8H_{17}$.

In certain embodiments, the invention relates to the aforementioned method, wherein $R_9$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)$═$C(R_8)_2$, —C≡$CR_8$, —$CH(R_8)_2$, or —$C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)$═$C(R_8)_2$, —C≡$CR_8$, —$CH(R_8)_2$, or —$C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)$═$C(R_8)_2$, —C≡$CR_8$, —$CH(R_8)_2$, or —$C(R_8)_3$.

In certain embodiments, the invention relates to the aforementioned method, wherein $R_9$ represents H, alkyl, fluoroalkyl, cycloalkyl, heterocycloalkyl, —$(CH_2)_n$—$R_8$, —$CH(R_8)_2$, or —$C(R_8)_3$;

$R_5$ represents H, alkyl, fluoroalkyl, cycloalkyl, heterocycloalkyl, —$(CH_2)_n$—$R_8$, —$CH(R_8)_2$, or —$C(R_8)_3$; and $R_6$ represents H, alkyl, fluoroalkyl, cycloalkyl, heterocycloalkyl, —$(CH_2)_n$—$R_8$, —$CH(R_8)_2$, or —$C(R_8)_3$.

In certain embodiments, the invention relates to the aforementioned method, wherein $R_9$ represents H, alkyl, fluoroalkyl, cycloalkyl, heterocycloalkyl, —$(CH_2)_n$—$R_8$, —$CH(R_8)_2$, or —$C(R_8)_3$;

$R_5$ represents H, alkyl, fluoroalkyl, cycloalkyl, heterocycloalkyl, —$(CH_2)_n$—$R_8$, —$CH(R_8)_2$, or —$C(R_8)_3$;

$R_6$ represents H, alkyl, fluoroalkyl, cycloalkyl, heterocycloalkyl, —$(CH_2)_n$—$R_8$, —$CH(R_8)_2$, or —$C(R_8)_3$;

X is C; and

Y is O.

In certain embodiments, the invention relates to the aforementioned method, wherein X is C;

Y is O; and $R_9$ is absent.

In certain embodiments, the invention relates to the aforementioned method, wherein X is C;

Y is O;

$R_9$ is absent; and z is 0 or 1.

In certain embodiments, the invention relates to the aforementioned method, wherein X is C;

Y is O;

$R_9$ is absent;

z is 0 or 1; and $R_5$ is H.

In certain embodiments, the invention relates to the aforementioned method, wherein X is C;

Y is O;

$R_9$ is absent;

z is 0 or 1;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein X is C;

Y is O;

$R_9$ is absent;

z is 0 or 1;

$R_5$ is H; and $R_6$ represents n-$C_4H_9$ or —$C_2H_4NH_2$.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

z is 0 or 1;

$R_5$ is H;

$R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$; and $R_9$ is absent.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

z is 0 or 1;

$R_5$ is H;

$R_6$ represents n-$C_4H_9$ or n-$C_6H_{13}$; and $R_9$ is absent.

In certain embodiments, the invention relates to the aforementioned method, wherein $R_1$, $R_3$, and $R_4$ are methyl;

$R_2$ is n-$C_8H_{17}$;

X is C;

Y is O;

z is 0 or 1;

$R_5$ is H;

$R_6$ represents n-$C_4H_9$ or n-$C_6H_{13}$; and $R_9$ is absent.

In certain embodiments, the invention relates to the aforementioned method, wherein X is C;

Y is O;

$R_9$ is absent; and z is 1.

In certain embodiments, the invention relates to the aforementioned method, wherein X is C;

Y is O;

$R_9$ is absent;

z is 1; and $R_5$ is H.

In certain embodiments, the invention relates to the aforementioned method, wherein X is C;

Y is O;

$R_9$ is absent;

z is 1;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein X is C;

Y is O;

$R_9$ is absent;

z is 1;

$R_5$ is H; and $R_6$ represents n-$C_4H_9$ or —$C_2H_4NH_2$.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

z is 1;

$R_5$ is H;

$R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$; and $R_9$ is absent.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

z is 1;

$R_5$ is H;

$R_6$ represents n-$C_4H_9$ or n-$C_6H_{13}$; and $R_9$ is absent.

In certain embodiments, the invention relates to the aforementioned method, wherein $R_1$, $R_3$, and $R_4$ are methyl;

$R_2$ is n-$C_8H_{17}$;

X is C;

Y is O;

z is 1;

$R_5$ is H;

$R_6$ represents n-$C_4H_9$ or n-$C_6H_{13}$; and $R_9$ is absent.

In certain embodiments, the invention relates to a method comprising the step of contacting a first gas with an ionic liquid, thereby generating a second gas; wherein said ionic liquid is represented by:

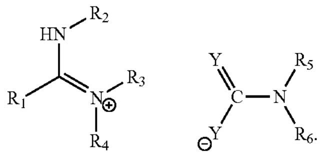

wherein said first gas is an inert gas;

said second gas is $CO_2$ or $CS_2$;

$R_1$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, or $—C(R_8)_3$;

$R_2$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, or $—C(R_8)_3$;

$R_3$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, or $—C(R_8)_3$;

$R_4$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, or $—C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, $—C(R_8)_3$, or $—(CH_2)_n—NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C≡CR_8$, $—CH(R_8)_2$, $—C(R_8)_3$, or $—(CH_2)_n—NH_2$;

Y represents independently for each occurrence O or S;

$R_8$ represents independently for each occurrence $—(CH_2)_n—CH_3$, cycloalkyl, aryl, or heteroaryl;

n represents independently for each occurrence an integer in the range 1-10 inclusive.

In certain embodiments, the invention relates to the aforementioned method, wherein said first gas is nitrogen;

$R_1$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$;

$R_2$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$;

$R_3$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$;

$R_4$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, or $—CH(R_8)_2$, or $—C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C≡CR_8$, $—CH(R_8)_2$, or $—C(R_8)_3$.

In certain embodiments, the invention relates to the aforementioned method, wherein said first gas is nitrogen;

$R_1$ represents H, alkyl, fluoroalkyl, cycloalkyl, heterocycloalkyl, $—(CH_2)_n—R_8$, $—CH(R_8)_2$, or $—C(R_8)_3$;

$R_2$ represents H, alkyl, fluoroalkyl, cycloalkyl, heterocycloalkyl, $—(CH_2)_n—R_8$, $—CH(R_8)_2$, or $—C(R_8)_3$;

$R_3$ represents H, alkyl, fluoroalkyl, cycloalkyl, heterocycloalkyl, $—(CH_2)_n—R_8$, $—CH(R_8)_2$, or $—C(R_8)_3$;

$R_4$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$; and $R_6$ represents H, alkyl, fluoroalkyl, cycloalkyl, heterocycloalkyl, $—(CH_2)_n—R_8$, $—CH(R_8)_2$, or $—C(R_8)_3$.

In certain embodiments, the invention relates to the aforementioned method, wherein said first gas is nitrogen;

$R_1$ represents H, alkyl, fluoroalkyl, cycloalkyl, heterocycloalkyl, $—(CH_2)_n—R_8$, $—CH(R_8)_2$, or $—C(R_8)_3$;

$R_2$ represents H, alkyl, fluoroalkyl, cycloalkyl, heterocycloalkyl, $—(CH_2)_n—R_8$, $—CH(R_8)_2$, or $—C(R_8)_3$;

$R_3$ represents H, alkyl, fluoroalkyl, cycloalkyl, heterocycloalkyl, $—(CH_2)_n—R_8$, $—CH(R_8)_2$, or $—C(R_8)_3$;

$R_4$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$;

$R_6$ represents H, alkyl, fluoroalkyl, cycloalkyl, heterocycloalkyl, $—(CH_2)_n—R_8$, $—CH(R_8)_2$, or $—C(R_8)_3$; and Y is O.

In certain embodiments, the invention relates to the aforementioned method, wherein said first gas is nitrogen; and Y is O.

In certain embodiments, the invention relates to the aforementioned method, wherein
said first gas is nitrogen;
Y is O; and
$R_1$, $R_3$, and $R_4$ are methyl.

In certain embodiments, the invention relates to the aforementioned method, wherein
said first gas is nitrogen;
Y is O;
$R_1$, $R_3$, and $R_4$ are methyl; and
$R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned method, wherein
said first gas is nitrogen;
Y is O;
$R_1$, $R_3$, and $R_4$ are methyl; and
$R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned method, wherein
said first gas is nitrogen;
Y is O;
$R_1$, $R_3$, and $R_4$ are methyl;
$R_2$ represents n-$C_4H_9$, n-$C_5H_{11}$, n-$C_6H_{13}$, n-$C_7H_{15}$, or n-$C_8H_{17}$; and
$R_5$ is H.

In certain embodiments, the invention relates to the aforementioned method, wherein
said first gas is nitrogen;
$R_1$, $R_3$, and $R_4$ are methyl,
$R_2$ represents n-$C_4H_9$, n-$C_5H_{11}$, n-$C_6H_{13}$, n-$C_7H_{15}$, or n-$C_8H_{17}$;
Y is O;
$R_5$ is H; and
$R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein
said first gas is nitrogen;
$R_1$, $R_3$, and $R_4$ are methyl;
$R_2$ is n-$C_8H_{17}$;
Y is O;
$R_5$ is H; and
$R_6$ represents n-$C_4H_9$ or n-$C_8H_{17}$.

In certain embodiments, the invention relates to the aforementioned method, wherein
said first gas is nitrogen;
$R_1$ represents H, alkyl, fluoroalkyl, cycloalkyl, heterocycloalkyl, —$(CH_2)_n$—$R_8$, —$CH(R_8)_2$, or —$C(R_8)_3$;
$R_2$ represents H, alkyl, fluoroalkyl, cycloalkyl, heterocycloalkyl, —$(CH_2)_n$—$R_8$, —$CH(R_8)_2$, or —$C(R_8)_3$;
$R_3$ represents H, alkyl, fluoroalkyl, cycloalkyl, heterocycloalkyl, —$(CH_2)_n$—$R_8$, —$CH(R_8)_2$, or —$C(R_8)_3$;
$R_4$ represents H, alkyl, fluoroalkyl, cycloalkyl, heterocycloalkyl, —$(CH_2)_n$—$R_8$, —$CH(R_8)_2$, or —$C(R_8)_3$;
$R_5$ represents H, alkyl, fluoroalkyl, cycloalkyl, heterocycloalkyl, —$(CH_2)_n$—$R_8$, —$CH(R_8)_2$, or —$C(R_8)_3$;
$R_6$ represents H, alkyl, fluoroalkyl, cycloalkyl, heterocycloalkyl, —$(CH_2)_n$—$R_8$, —$CH(R_8)_2$, or —$C(R_8)_3$; and
Y is S.

In certain embodiments, the invention relates to the aforementioned method, wherein
said first gas is nitrogen; and
Y is S.

In certain embodiments, the invention relates to the aforementioned method, wherein
said first gas is nitrogen;
Y is S; and
$R_1$, $R_3$, and $R_4$ are methyl.

In certain embodiments, the invention relates to the aforementioned method, wherein
said first gas is nitrogen;
Y is S;
$R_1$, $R_3$, and $R_4$ are methyl; and
$R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned method, wherein
said first gas is nitrogen;
Y is S;
$R_1$, $R_3$, and $R_4$ are methyl; and
$R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned method, wherein
said first gas is nitrogen;
Y is S;
$R_1$, $R_3$, and $R_4$ are methyl;
$R_2$ represents n-$C_4H_9$, n-$C_5H_{11}$, n-$C_6H_{13}$, n-$C_7H_{15}$, or n-$C_8H_{17}$; and
$R_5$ is H.

In certain embodiments, the invention relates to the aforementioned method, wherein
said first gas is nitrogen;
$R_1$, $R_3$, and $R_4$ are methyl,
$R_2$ represents n-$C_4H_9$, n-$C_5H_{11}$, n-$C_6H_{13}$, n-$C_7H_{15}$, or n-$C_8H_{17}$;
Y is S;
$R_5$ is H; and
$R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein
said first gas is nitrogen;
$R_1$, $R_3$, and $R_4$ are methyl;
$R_2$ is n-$C_8H_{17}$;
Y is S;
$R_5$ is H; and
$R_6$ represents n-$C_4H_9$ or n-$C_8H_{17}$.

In certain embodiments, the invention relates to the aforementioned method, wherein said ionic liquid is represented by

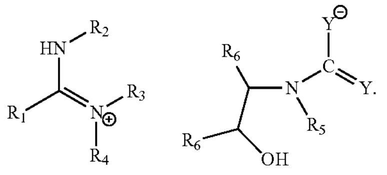

In certain embodiments, the invention relates to the aforementioned method, wherein said ionic liquid is represented by

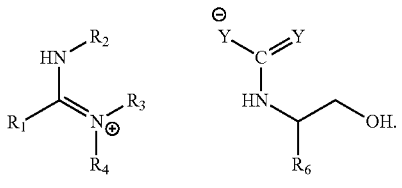

In certain embodiments, the invention relates to the aforementioned method, wherein said ionic liquid is represented by

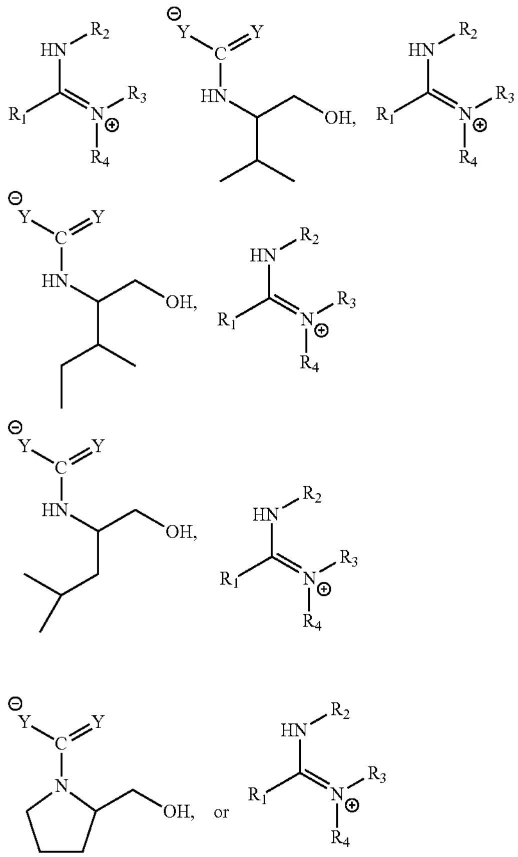

or

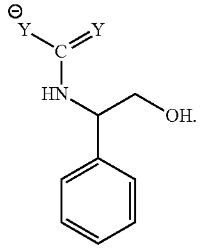

In certain embodiments, the invention relates to the aforementioned method, wherein said ionic liquid is represented by

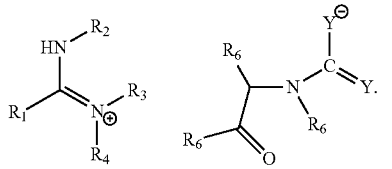

In certain embodiments, the invention relates to the aforementioned method, wherein said ionic liquid is represented by

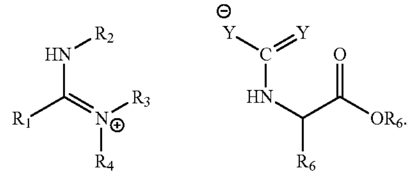

In certain embodiments, the invention relates to the aforementioned method, wherein said ionic liquid is represented by

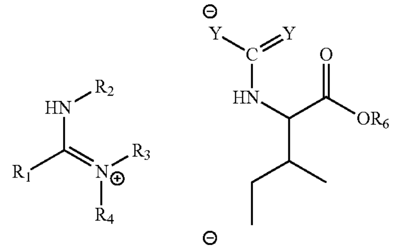

or

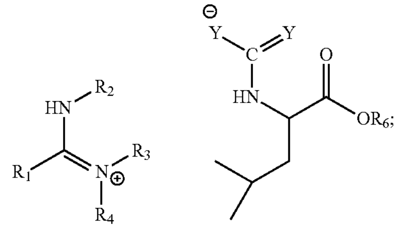

wherein $R_6$ is represented by n-$C_8H_{17}$ or n-$C_{18}H_{37}$.

In certain embodiments, the invention relates to the aforementioned method, wherein said ionic liquid is represented by

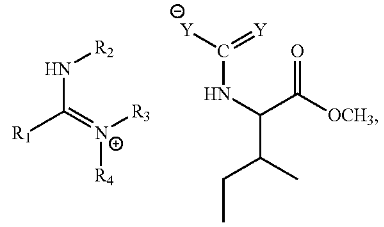

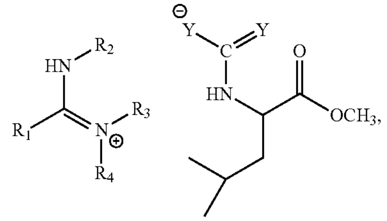

or

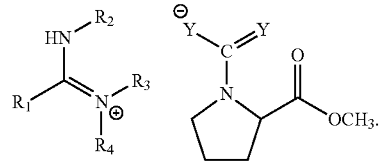

In certain embodiments, the invention relates to a method comprising the step of contacting a first gas with an ionic liquid, thereby generating a second gas; wherein said ionic liquid is represented by:

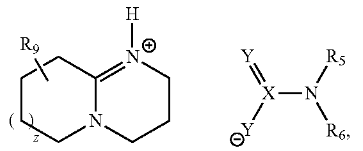

wherein said first gas is an inert gas;

said second gas is $CO_2$ or $CS_2$;

$R_9$ is absent or represents one or more substituents attached to the ring, each of which is independently selected from the group consisting of H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C\equiv CR_8$, $—CH(R_8)_2$, $—C(R_8)_3$, and $—(CH_2)_n—NH_2$;

z is zero or an integer in the range of 1 to 3;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C\equiv CR_8$, $—CH(R_8)_2$, $—C(R_8)_3$, or $—(CH_2)_n—NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C\equiv CR_8$, $—CH(R_8)_2$, $—C(R_8)_3$, or $—(CH_2)_n—NH_2$;

Y represents independently for each occurrence O or S;

$R_8$ represents independently for each occurrence $—(CH_2)_n—CH_3$, cycloalkyl, aryl, or heteroaryl; and n represents independently for each occurrence an integer in the range 1-10 inclusive.

In certain embodiments, the invention relates to the aforementioned method, wherein said first gas is nitrogen;

$R_9$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C\equiv CR_8$, $—CH(R_8)_2$, or $—C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C\equiv CR_8$, $—CH(R_8)_2$, or $—C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)=C(R_8)_2$, $—C\equiv CR_8$, $—CH(R_8)_2$, or $—C(R_8)_3$.

In certain embodiments, the invention relates to the aforementioned method, wherein said first gas is nitrogen;

$R_9$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$; and $R_6$ represents H, alkyl, fluoroalkyl, cycloalkyl, heterocycloalkyl, $—(CH_2)_n—R_8$, $—CH(R_8)_2$, or $—C(R_8)_3$.

In certain embodiments, the invention relates to the aforementioned method, wherein said first gas is nitrogen;

$R_9$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$;

$R_6$ represents H, alkyl, fluoroalkyl, cycloalkyl, heterocycloalkyl, $—(CH_2)_n—R_8$, $—CH(R_8)_2$, or $—C(R_8)_3$; and Y is O.

In certain embodiments, the invention relates to the aforementioned method, wherein said first gas is nitrogen; and Y is O.

In certain embodiments, the invention relates to the aforementioned method, wherein said first gas is nitrogen;

Y is O; and $R_9$ is absent.

In certain embodiments, the invention relates to the aforementioned method, wherein said first gas is nitrogen;

Y is O;

$R_9$ is absent; and z is 0 or 1.

In certain embodiments, the invention relates to the aforementioned method, wherein said first gas is nitrogen;

Y is O;

$R_9$ is absent;

z is 0 or 1; and $R_5$ is H.

In certain embodiments, the invention relates to the aforementioned method, wherein said first gas is nitrogen;

Y is O;

$R_9$ is absent;

z is 0 or 1;

$R_5$ is H; and $R_6$ represents n-$C_4H_9$, sec-$C_4H_9$, t-$C_4H_9$, cyclohexyl, n-$C_6H_{13}$, n-$C_8H_{17}$, $—C_2H_4NH_2$, or $—C_6H_{12}NH_2$.

In certain embodiments, the invention relates to the aforementioned method, wherein said first gas is nitrogen;

Y is O;

$R_9$ is absent;

z is 0 or 1;

$R_5$ is H; and $R_6$ represents n-$C_4H_9$ or $—C_2H_4NH_2$.

In certain embodiments, the invention relates to the aforementioned method, wherein said first gas is nitrogen;

$R_9$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$;

$R_6$ represents H, alkyl, fluoroalkyl, cycloalkyl, heterocycloalkyl, $—(CH_2)_n—R_8$, $—CH(R_8)_2$, or $—C(R_8)_3$; and Y is S.

In certain embodiments, the invention relates to the aforementioned method, wherein said first gas is nitrogen; and Y is S.

In certain embodiments, the invention relates to the aforementioned method, wherein said first gas is nitrogen;

Y is S; and $R_9$ is absent.

In certain embodiments, the invention relates to the aforementioned method, wherein said first gas is nitrogen;

Y is S;

$R_9$ is absent; and z is 0 or 1.

In certain embodiments, the invention relates to the aforementioned method, wherein said first gas is nitrogen;

Y is S;

$R_9$ is absent;

z is 0 or 1; and $R_5$ is H.

In certain embodiments, the invention relates to the aforementioned method, wherein said first gas is nitrogen;

Y is S;

$R_9$ is absent;

z is 0 or 1;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein said first gas is nitrogen;

Y is S;

$R_9$ is absent;

z is 0 or 1;

$R_5$ is H; and $R_6$ represents n-$C_4H_9$ or —$C_2H_4NH_2$.

In certain embodiments, the invention relates to the aforementioned method, wherein said ionic liquid is represented by

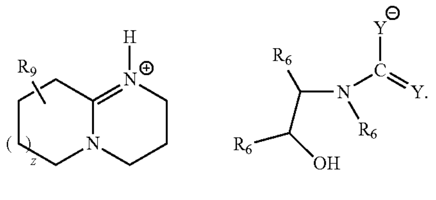

In certain embodiments, the invention relates to the aforementioned method, wherein said ionic liquid is represented by

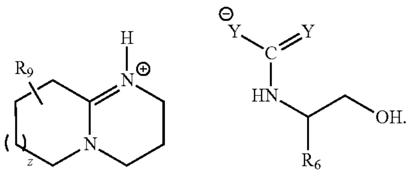

In certain embodiments, the invention relates to the aforementioned method, wherein said ionic liquid is represented by

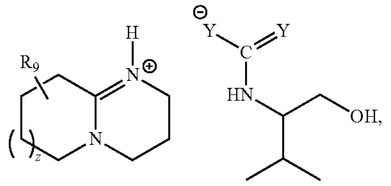

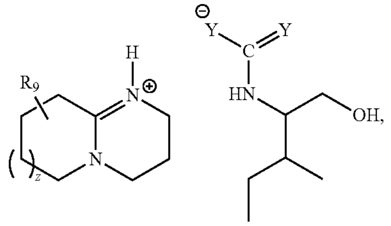

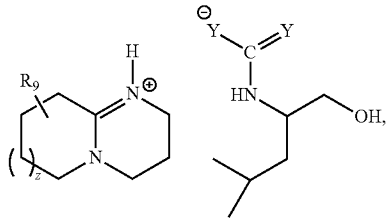

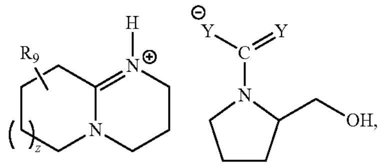

or

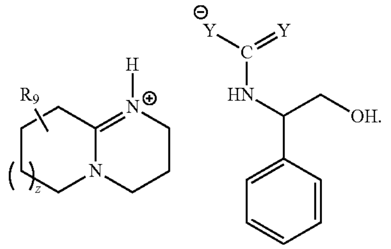

In certain embodiments, the invention relates to the aforementioned method, wherein said ionic liquid is represented by

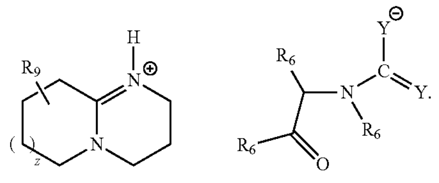

In certain embodiments, the invention relates to the aforementioned method, wherein said ionic liquid is represented by

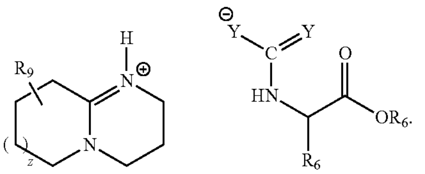

In certain embodiments, the invention relates to the aforementioned method, wherein said ionic liquid is represented by

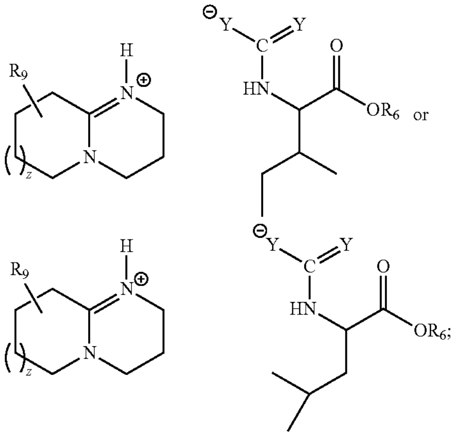

or wherein $R_6$ is represented by n-$C_8H_{17}$ or n-$C_{18}H_{37}$.

In certain embodiments, the invention relates to the aforementioned method, wherein said ionic liquid is represented by

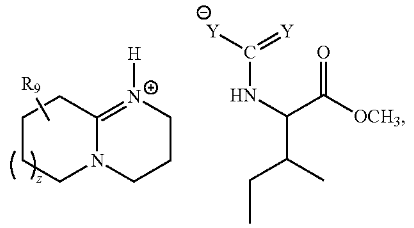

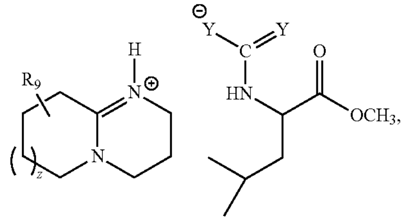

or

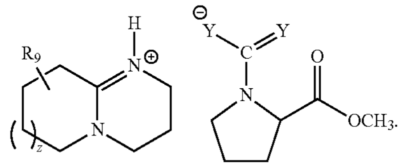

In certain embodiments, the invention relates to a method of removing a gas from a mixture, comprising the step of contacting said mixture with a first compound and a second compound, wherein said first compound is selected from the group consisting of

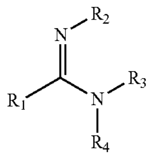

and

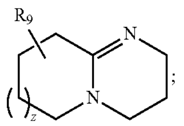

;

wherein $R_1$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$OR_8$, —$N(R_8)_2$, —$SR_8$, —C(═O)$OR_8$, —OC(═O)$R_8$, —$NR_8$C(═O)$R_8$, —C(═O)$N(R_8)_2$, —C(═O)$SR_8$, —SC(═O)$R_8$, —S(═O)$R_8$, —S(═O)$_2R_8$, —S(═O)$_2OR_8$, —C(═O)$R_8$, —C(═$NR_8$)$R_8$, —C(═S)$R_8$, —C($R_8$)═C$(R_8)_2$, —C≡C$R_8$, —CH$(R_8)_2$, or —C$(R_8)_3$;

$R_2$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$OR_8$, —$N(R_8)_2$, —$SR_8$, —C(═O)$OR_8$, —OC(═O)$R_8$, —$NR_8$C(═O)$R_8$, —C(═O)$N(R_8)_2$, —C(═O)$SR_8$, —SC(═O)$R_8$, —S(═O)$R_8$, —S(═O)$_2R_8$, —S(═O)$_2OR_8$, —C(═O)$R_8$, —C(═$NR_8$)$R_8$, —C(═S)$R_8$, —C($R_8$)═C$(R_8)_2$, —C≡C$R_8$, —CH$(R_8)_2$, or —C$(R_8)_3$;

$R_3$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$OR_8$, —$N(R_8)_2$, —$SR_8$, —C(═O)$OR_8$, —OC(═O)$R_8$, —$NR_8$C(═O)$R_8$, —C(═O)$N(R_8)_2$, —C(═O)$SR_8$, —SC(═O)$R_8$, —S(═O)$R_8$, —S(═O)$_2R_8$, —S(═O)$_2OR_8$, —C(═O)$R_8$, —C(═$NR_8$)$R_8$, —C(═S)$R_8$, —C($R_8$)═C$(R_8)_2$, —C≡C$R_8$, —CH$(R_8)_2$, or —C$(R_8)_3$;

$R_4$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$OR_8$, —$N(R_8)_2$, —$SR_8$, —C(═O)$OR_8$, —OC(═O)$R_8$, —$NR_8$C(═O)$R_8$, —C(═O)$N(R_8)_2$, —C(═O)$SR_8$, —SC(═O)$R_8$, —S(═O)$R_8$, —S(═O)$_2R_8$, —S(═O)$_2OR_8$, —C(═O)$R_8$, —C(═$NR_8$)$R_8$, —C(═S)$R_8$, —C($R_8$)═C$(R_8)_2$, —C≡C$R_8$, —CH$(R_8)_2$, or —C$(R_8)_3$;

$R_8$ represents independently for each occurrence —$(CH_2)_n$—$CH_3$, cycloalkyl, aryl, or heteroaryl; and n represents independently for each occurrence an integer in the range 1-10 inclusive;

$R_9$ is absent or represents one or more substituents attached to the ring, each of which is independently selected from the group consisting of H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$OR_8$, —$N(R_8)_2$, —$SR_8$, —C(═O)$OR_8$, —OC(═O)$R_8$, —$NR_8$C(═O)$R_8$, —C(═O)$N(R_8)_2$, —C(═O)$SR_8$, —SC(═O)$R_8$, —S(═O)$R_8$, —S(═O)$_2R_8$, —S(═O)$_2OR_8$, —C(═O)$R_8$, —C(═$NR_8$)$R_8$, —C(═S)$R_8$, —C($R_8$)═C$(R_8)_2$, —C≡C$R_8$, —CH$(R_8)_2$, —C$(R_8)_3$, or —$(CH_2)_n$—$NH_2$;

z is zero or an integer in the range of 1 to 3; and said second compound is represented by

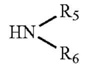

wherein $R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, $-C(R_8)_3$, or $-(CH_2)_n-NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-SC(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, $-C(R_8)_3$, or $-(CH_2)_n-NH_2$;

$R_8$ represents independently for each occurrence cycloalkyl, aryl, or heteroaryl;

n represents independently for each occurrence an integer in the range 1-10 inclusive; and said gas is represented by:

$$Y=X=Y$$

wherein

X represents C or N; and

Y represents independently for each occurrence O or S.

In certain embodiments, the invention relates to the aforementioned method, wherein $R_1$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$;

$R_2$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$;

$R_3$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$;

$R_4$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, or $-CH(R_8)_2$, or $-C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-C(R_8)=C(R_8)_2$, $-C\equiv CR_8$, $-CH(R_8)_2$, or $-C(R_8)_3$.

In certain embodiments, the invention relates to the aforementioned method, wherein $R_1$ represents H, alkyl, fluoroalkyl, cycloalkyl, heterocycloalkyl, $-(CH_2)_n-R_8$, $-CH(R_8)_2$, or $-C(R_8)_3$;

$R_2$ represents H, alkyl, fluoroalkyl, cycloalkyl, heterocycloalkyl, $-(CH_2)_n-R_8$, $-CH(R_8)_2$, or $-C(R_8)_3$;

$R_3$ represents H, alkyl, fluoroalkyl, cycloalkyl, heterocycloalkyl, $-(CH_2)_n-R_8$, $-CH(R_8)_2$, or $-C(R_8)_3$;

$R_4$ represents H, alkyl, fluoroalkyl, cycloalkyl, heterocycloalkyl, $-(CH_2)_n-R_8$, $-CH(R_8)_2$, or $-C(R_8)_3$;

$R_5$ represents H, alkyl, fluoroalkyl, cycloalkyl, heterocycloalkyl, $-(CH_2)_n-R_8$, $-CH(R_8)_2$, or $-C(R_8)_3$; and $R_6$ represents H, alkyl, fluoroalkyl, cycloalkyl, heterocycloalkyl, $-(CH_2)_n-R_8$, $-CH(R_8)_2$, or $-C(R_8)_3$.

In certain embodiments, the invention relates to the aforementioned method, wherein $R_1$ represents H, alkyl, fluoroalkyl, cycloalkyl, heterocycloalkyl, $-(CH_2)_n-R_8$, $-CH(R_8)_2$, or $-C(R_8)_3$;

$R_2$ represents H, alkyl, fluoroalkyl, cycloalkyl, heterocycloalkyl, $-(CH_2)_n-R_8$, $-CH(R_8)_2$, or $-C(R_8)_3$;

$R_3$ represents H, alkyl, fluoroalkyl, cycloalkyl, heterocycloalkyl, $-(CH_2)_n-R_8$, $-CH(R_8)_2$, or $-C(R_8)_3$;

$R_4$ represents H, alkyl, fluoroalkyl, cycloalkyl, heterocycloalkyl, $-(CH_2)_n-R_8$, $-CH(R_8)_2$, or $-C(R_8)_3$;

$R_5$ represents H, alkyl, fluoroalkyl, cycloalkyl, heterocycloalkyl, $-(CH_2)_n-R_8$, $-CH(R_8)_2$, or $-C(R_8)_3$;

$R_6$ represents H, alkyl, fluoroalkyl, cycloalkyl, heterocycloalkyl, $-(CH_2)_n-R_8$, $-CH(R_8)_2$, or $-C(R_8)_3$; and Y is O.

In certain embodiments, the invention relates to the aforementioned method, wherein said second compound is represented by

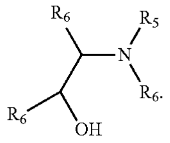

In certain embodiments, the invention relates to the aforementioned method, wherein said second compound is represented by

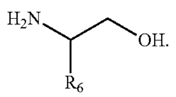

In certain embodiments, the invention relates to the aforementioned method, wherein said second compound is selected from the group consisting of prolinol, leucinol, isoleucinol, valinol, and norephedrine.

In certain embodiments, the invention relates to the aforementioned method, wherein said second compound is represented by

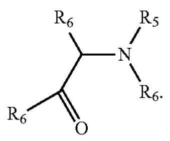

In certain embodiments, the invention relates to the aforementioned method, wherein said second compound is represented by

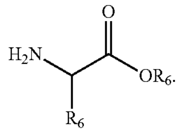

In certain embodiments, the invention relates to the aforementioned method, wherein said second compound is selected from the group consisting of leucine octyl ester, isoleucine octyl ester, leucine octadecyl ester, and isoleucine octadecyl ester.

In certain embodiments, the invention relates to the aforementioned method, wherein said second compound is selected from the group consisting of leucine proline methyl ester, leucine methyl ester, and isoleucine methyl ester.

In certain embodiments, the invention relates to the aforementioned method, wherein X is C;

Y is S;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is S;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein X is C; and Y is O.

In certain embodiments, the invention relates to the aforementioned method, wherein X is C;

Y is O; and $R_1$, $R_3$, and $R_4$ are methyl.

In certain embodiments, the invention relates to the aforementioned method, wherein X is C;

Y is O;

$R_1$, $R_3$, and $R_4$ are methyl; and $R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned method, wherein X is C;

Y is O;

$R_1$, $R_3$, and $R_4$ are methyl; and $R_2$ represents n-$C_4H_9$, n-$C_5H_{11}$, n-$C_6H_{13}$, n-$C_7H_{15}$, or n-$C_8H_{17}$.

In certain embodiments, the invention relates to the aforementioned method, wherein X is C;

Y is O;

$R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$; and $R_5$ is H.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein $R_1$, $R_3$, and $R_4$ are methyl;

$R_2$ is n-$C_8H_{17}$;

X is C;

Y is O;

$R_5$ is H; and $R_6$ represents n-$C_4H_9$ or n-$C_8H_{17}$.

In certain embodiments, the invention relates to the aforementioned method, wherein $R_9$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)$=$C(R_8)_2$, —C≡$CR_8$, —$CH(R_8)_2$, or —$C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)$=$C(R_8)_2$, —C≡$CR_8$, —$CH(R_8)_2$, or —$C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —$(CH_2)_n$—$R_8$, —$C(R_8)$=$C(R_8)_2$, —C≡$CR_8$, —$CH(R_8)_2$, or —$C(R_8)_3$.

In certain embodiments, the invention relates to the aforementioned method, wherein $R_9$ represents H, alkyl, fluoroalkyl, cycloalkyl, heterocycloalkyl, —$(CH_2)_n$—$R_8$, —$CH(R_8)_2$, or —$C(R_8)_3$;

$R_5$ represents H, alkyl, fluoroalkyl, cycloalkyl, heterocycloalkyl, —$(CH_2)_n$—$R_8$, —$CH(R_8)_2$, or —$C(R_8)_3$; and $R_6$ represents H, alkyl, fluoroalkyl, cycloalkyl, heterocycloalkyl, —$(CH_2)_n$—$R_8$, —$CH(R_8)_2$, or —$C(R_8)_3$.

In certain embodiments, the invention relates to the aforementioned method, wherein $R_9$ represents H, alkyl, fluoroalkyl, cycloalkyl, heterocycloalkyl, —$(CH_2)_n$—$R_8$, —$CH(R_8)_2$, or —$C(R_8)_3$;

$R_5$ represents H, alkyl, fluoroalkyl, cycloalkyl, heterocycloalkyl, —$(CH_2)_n$—$R_8$, —$CH(R_8)_2$, or —$C(R_8)_3$;

$R_6$ represents H, alkyl, fluoroalkyl, cycloalkyl, heterocycloalkyl, —$(CH_2)_n$—$R_8$, —$CH(R_8)_2$, or —$C(R_8)_3$;

X is C; and

Y is O.

In certain embodiments, the invention relates to the aforementioned method, wherein X is C;

Y is O; and $R_9$ is absent.

In certain embodiments, the invention relates to the aforementioned method, wherein X is C;

Y is O;

$R_9$ is absent; and z is 0 or 1.

In certain embodiments, the invention relates to the aforementioned method, wherein X is C;

Y is O;

$R_9$ is absent;

z is 0 or 1; and $R_5$ is H.

In certain embodiments, the invention relates to the aforementioned method, wherein X is C;

Y is O;

$R_9$ is absent;

z is 0 or 1;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein X is C;

Y is O;

$R_9$ is absent;

z is 0 or 1;

$R_5$ is H; and $R_6$ represents n-$C_4H_9$ or —$C_2H_4NH_2$.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

z is 0 or 1;

$R_5$ is H;

$R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$; and $R_9$ is absent.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

z is 0 or 1;

$R_5$ is H;

$R_6$ represents n-$C_4H_9$ or n-$C_6H_{13}$; and $R_9$ is absent.

In certain embodiments, the invention relates to the aforementioned method, wherein $R_1$, $R_3$, and $R_4$ are methyl;

$R_2$ is n-$C_8H_{17}$;

X is C;

Y is O;

z is 0 or 1;

$R_5$ is H;

$R_6$ represents n-$C_4H_9$ or n-$C_6H_{13}$; and $R_9$ is absent.

In certain embodiments, the invention relates to the aforementioned method, wherein X is C;

Y is O;

$R_9$ is absent; and z is 1.

In certain embodiments, the invention relates to the aforementioned method, wherein X is C;

Y is O;

$R_9$ is absent;

z is 1; and $R_5$ is H.

In certain embodiments, the invention relates to the aforementioned method, wherein X is C;

Y is O;

$R_9$ is absent;

z is 1;

$R_5$ is H; and $R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$.

In certain embodiments, the invention relates to the aforementioned method, wherein X is C;

Y is O;

$R_9$ is absent;

z is 1;

$R_5$ is H; and $R_6$ represents n-$C_4H_9$ or —$C_2H_4NH_2$.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

z is 1;

$R_5$ is H;

$R_6$ represents n-$C_4H_9$, sec-$C_4H_9$, t-$C_4H_9$, cyclohexyl, n-$C_6H_{13}$, n-$C_8H_{17}$, —$C_2H_4NH_2$, or —$C_6H_{12}NH_2$; and $R_9$ is absent.

In certain embodiments, the invention relates to the aforementioned method, wherein $R_1$, $R_3$, and $R_4$ are methyl;

$R_2$ represents n-$C_4H_9$, n-$C_5H_{11}$, n-$C_6H_{13}$, n-$C_7H_{15}$, or n-$C_8H_{17}$;

X is C;

Y is O;

z is 1;

$R_5$ is H;

$R_6$ represents n-$C_4H_9$ or n-$C_6H_{13}$; and $R_9$ is absent.

In certain embodiments, the invention relates to the aforementioned method, wherein $R_1$, $R_3$, and $R_4$ are methyl;

$R_2$ is n-$C_8H_{17}$;

X is C;

Y is O;

z is 1;

$R_5$ is H;

$R_6$ represents n-$C_4H_9$ or n-$C_6H_{13}$; and $R_9$ is absent.

Exemplary Embodiments (i). Compounds

Useful compounds will be described below using various formulas. In each case, the variables in the formula are defined specifically for each individual formula. A definition of a variable for one formula should not be used to vary a definition provided for another formula, although a variable that has not been defined for one formula may be interpreted by analogy with a definition elsewhere for a similar formula.

Variations, modifications, and other implementations of what is described herein will occur to those of ordinary skill without departing from the spirit and the scope of the invention. Accordingly, the invention is not to be limited only to the preceding illustrative description. For additional illustrative features that may be used with the invention, including the embodiments described here, refer to the documents listed herein above and incorporated by reference in their entirety. All operative combinations between the above described illustrative embodiments and those features described below are considered to be potentially patentable embodiments of the invention.

EXEMPLIFICATION

The invention now being generally described, it will be more readily understood by reference to the following examples which are included merely for purposes of illustration of certain aspects and embodiments of the present invention, and are not intended to limit the invention.

Example 1

N,N-Dimethyl-N'-butyl Ethanimidamide (A or C4)

Dimethylcarbamyl chloride (9.35 g, 86.9 mmol) was slowly added to a solution of N-hexyl acetamide (10.0 g, 86.9 mmol) in 10 mL of dry toluene. After being refluxed under a nitrogen atmosphere for 16 h, the volatile materials were removed on a rotary evaporator and then in vacuo for 2 h at room temperature. The residue was dissolved in 30 mL dichloromethane and the solution was stirred vigorously with a solution of 3.48 g (86.9 mmol) of sodium hydroxide in 40 mL water for 30 min. Calcium carbonate (3.48 g) was added to the mixture and it was stirred another 30 min. The organic phase was separated and the aqueous phase was washed with dichloromethane (3×25 mL). The combined organic phases were dried over anhydrous calcium carbonate. The volatile materials were evaporated on a rotary evaporator. The residue was distilled, bp 28-30° C./0.25 Torr (lit. bp 69-71° C./13 Torr (see Haug, E. et al. *Synthesis,* 1983, 35-37)), to yield 4.0 g (32%) of product, 98% pure (GC). IR (neat) 2956, 2929, 286 (C—H), 1629 (N═C) $cm^{-1}$. $^1H$ NMR 3.17 (t, 2H, $J_{HH}$ 7.2 Hz, —$\underline{H}$C$_2$—N═), 2.86 (s, 6H, —N—(C$\underline{H}_3$)$_2$); 1.87 (s, 3H, —N═C(C$\underline{H}_3$)—N); 1.5 (m, 2H, —C$\underline{H}_2$—CH$_2$—N═); 1.25- 1.4 (m, 6H, CH$_3$—(C$\underline{H}_2$)$_3$—); 0.88 (t, 3H, $J_{HH}$ 7.2 Hz, C$\underline{H}_3$).

Example 2

N,N-Dimethyl-N'-amyl ethanimidamide (B or C5)

N-Hexyl acetamide (10.0 g, 77.5 mmol) was added 10 mL of dry toluene, then 8.33 g (77.5 mmol) of dimethylcarbamyl chloride was slowly added and then refluxed under a nitrogen atmosphere for 16 h. The volatile materials were removed on a rotary evaporator and then in vacuo at room temperature. The residue was dissolved dichloromethane (30 mL) and 3.1 g (77.5 mmol) of sodium hydroxide dissolved aqueous solution (40 mL) was added. The mixture was stirred vigorously for 30 min. Calcium carbonate (3.1 g) was added to the mixture and it was stirred another 30 min. The organic phase was separated and the aqueous phase was washed with dichloromethane (3×25 mL). The combined organic liquids were dried (calcium carbonate) and the volatile materials were removed on a rotary evaporator. The residue was distilled at 40-41° C./0.25 Torr to yield 4.7 g (39%) of product (98.5% pure by GC). IR (neat) 2956, 2927, 2857 (C—H), 1626 (N═C) $cm^{-1}$. $^1H$ NMR 3.18 (t, 2H, $J_{HH}$ 7.5 Hz, —C$\underline{H}_2$—N═), 2.87 (s, 6H, —N—(C$\underline{H}_3$)$_2$); 1.88 (s, 3H, —N═C(C$\underline{H}_3$)—N); 1.51 (m, 2H, —C$\underline{H}_2$—CH$_2$—N═); 1.25-1.4 (m, 4H, CH$_3$—(C$\underline{H}_2$)$_2$—); 0.90 (t, 3H, $J_{HH}$ 6.9 Hz, C$\underline{H}_3$). $^{13}C$ NMR 158.90; 50.35; 38.15; 32.27; 29.98; 22.87; 14.31; 12.53.

Example 3

N,N-Dimethyl-N'-hexyl Ethanimidamide (C or C6)

To a solution of N-hexyl acetamide (15.0 g, 105 mmol) in 15 mL of dry toluene was slowly added 11.2 g (104.9 mmol) of dimethylcarbamyl chloride. The solution was refluxed under a nitrogen atmosphere for 24 h. The volatile materials were removed on a rotary evaporator and then in vacuo at room temperature. The residue was dissolved 30 mL of chloroform and stirred vigorously with a solution of 4.2 g sodium hydroxide in 40 mL of water for 30 min. Calcium carbonate (4.2 g) was added and stirring was continued for another 30 min. The organic phase was separated and the aqueous phase was extracted with dichloromethane (25 mL×3). The combined organic phases were dried (calcium carbonate) and the solvent was removed on a rotary evaporator. The residue was distilled at 52-54° C./0.25 Torr (lit. bp 125° C./30 Torr (see Oszczapowicz, J.; Raczynska, E. *J. Chem. Soc., Perkin Trans.* 2 1984, 1643-1666)) product to yield 8.7 g (49%) of liquid (purity 99% by GC). IR (neat) 2955, 2926, 2856 (C—H), 1626 (N═C) $cm^{-1}$. $^1H$ NMR 3.18 (t, 2H, $J_{HH}$ 7.5 Hz, —C$\underline{H}_2$—N═), 2.87 (s, 6H, —N—(C$\underline{H}_3$)$_2$); 1.87 (s, 3H, —N═C(C$\underline{H}_3$)—N); 1.49 (m, 2H, —C$\underline{H}_2$—CH$_2$—N═); 1.25-1.4 (m, 6H, CH$_3$—(C$\underline{H}_2$)$_3$—); 0.88 (t, 3H, $J_{HH}$ 7.2 Hz, C$\underline{H}_3$). $^{13}C$ NMR 158.79; 50.32; 38.07; 32.49; 32.00; 27.38; 22.80; 14.17; 12.45.

Example 4

N,N-Dimethyl-N'-heptyl Ethanimidamide (D or C7)

Dimethylcarbamyl chloride (6.86 g, 63.7 mmol) was added slowly to 10.0 g (63.7 mmol) of N-octyl acetamide in 10 mL of dry toluene and the solution was refluxed under a nitrogen atmosphere for 16 h. The volatile materials were removed on a rotary evaporator in vacuo. The residue, dissolved 30 mL of dichloromethane, was stirred vigorously with a solution of 2.55 g (63.7 mmol) of sodium hydroxide in 40 mL of water for 30 min. Calcium carbonate (2.55 g) was added to the mixture and stirring was continued for an additional 30 min. The organic phase was separated and the aqueous phase was extracted with dichloromethane (30 mL×3). The combined organic phases were dried (calcium carbonate) and the solvent was removed on a rotary evaporator. The residue was distilled at 63-64° C./0.25 Torr to yield 6.2 g (53%) of product (purity 99% by GC). IR 2956, 2925, 2854 (C—H), 1626 (N═C) $cm^{-1}$. $^1H$ NMR 3.17 (t, 2H, $J_{HH}$ 7.5 Hz, —C$\underline{H}_2$—N═), 2.86 (s, 6H, —N—(C$\underline{H}_3$)$_2$); 1.87 (s, 3H, —N═C(C$\underline{H}_3$)—N); 1.5 (m, 2H, —C$\underline{H}_2$—CH$_2$—N═); 1.25-1.4 (m, 10H, CH$_3$—(C$\underline{H}_2$)$_5$—); 0.88 (t, 3H, $J_{HH}$ 7.2 Hz, C$\underline{H}_3$).

Example 5

N,N-Dimethyl-N'-octyl Ethanimidamide (E or C8)

Dimethylcarbamyl chloride (6.29 g, 58.4 mmol) was added slowly to 10.0 g (58.4 mmol) of N-octyl acetamide in 10 mL of dry toluene and the solution was refluxed under a nitrogen atmosphere for 16 h. The volatile materials were removed on a rotary evaporator and in vacuo. The residue, dissolved dichloromethane (30 mL), was stirred strongly for 30 min with a solution of 2.34 g (58.4 mmol) of sodium hydroxide in 40 mL of water. Calcium carbonate (2.34 g) was added to the mixture and it was stirred an additional 30 min. The organic phase was separated and the aqueous phase was washed with dichloromethane (30 mL×3). The combined organic phases were dried (calcium carbonate) and the volatile materials were removed on a rotary evaporator. The residue was distilled at 72-77° C./0.25 Torr to yield 7.1 g (61%) of product (purity 99% by GC). IR (neat) 2955, 2924, 2853 (C—H), 1627 (N═C) $cm^{-1}$. $^1$H NMR 3.17 (t, 2H, $J_{HH}$ 6.9 Hz, —C$\underline{H}_2$—N═), 2.86 (s, 6H, —N—(C$\underline{H}_3$)$_2$); 1.87 (s, 3H, —N═C(C$\underline{H}_3$)—N); 1.5 (m, 2H, —$CH_2$—$CH_2$—N═); 1.25-1.4 (m, 10H, $CH_3$—(C$\underline{H}_2$)$_5$—); 0.88 (t, 3H, $J_{HH}$ 6.1 Hz, C$\underline{H}_3$).

Example 6

1-(p-Dimethylaminophenyl)-2-nitroethylene (DAPNE)

A mixture of 4-dimethylaminobenzaldehyde (1.5 g, 10 mmol) in 3 mL methanol, 0.61 g (10 mmol) nitrobenzene and 0.15 mL of 22% methylamine aqueous solution was stirred for 3 days. The dark red solid obtained after filtration was recrystallized from nitromethane and rinsed with cold methanol to yield 0.79 g (41.1%) of red crystals, mp 180.6-180.9° C. (ref mp 181° C. (see Richter-Egger, D. L. et al. *J. Chem. Educ.* 2001, 78, 1375-1378)). $^1$H NMR 3.08 (s, 6H, Ar—N($CH_3$)$_2$); 6.68 (2H, d, $J_{HH}$ 8.7 Hz, Ar—H); 7.43 (2H, d, $J_{HH}$ 9.0 Hz, Ar—H); 7.50 (1H, d, $J_{HH}$ 13.2 Hz, Ar—C$\underline{H}$); 7.97 (1H, d, $J_{HH}$ 13.5 Hz, C$\underline{H}$—$NO_2$).

Example 7

Preparation of Ionic Liquids and Their Reconversion to Amidine/Amine Mixtures Dry $CO_2$ gas was bubbled for 1 h through a solution of neat amidine and amine in a glass vessel immersed in a room-temperature water bath; the uptake of $CO_2$ is slightly exothermic. Amidine/1,6-diaminohexane (8) samples were heated until 8 dissolved completely and then $CO_2$ gas was bubbled through the sample mixtures.

An aliquot of 0.1 mL of E+5 was added to 0.9 mL of n-decane. Dry $CO_2$ was bubbled through the liquid for 30 min. Separation into 2 liquid phases (ca. 0.1 mL and 0.9 mL each) was observed after the cloudy mixture was allowed to stand undisturbed for some time. Then, $N_2$ gas was bubbled through the mixture for 2.5 h at 24° C. and one clear liquid phase was observed again.

Example 8

Measurements of $CO_2$ Uptake

A burette was filled with $CO_2$ gas and the apparatus was purged by flushing $CO_2$ through it for >30 min. Then, a flask with a weighed amount of amidine and amine mixture (neat) was attached to gas burette. The sample liquid was stirred with a Teflon-coated spin bar and the volume of $CO_2$ taken up was recorded as a function of time until no change was discernible. This procedure was repeated 3 times on different aliquots of each sample.

The percentage of the theoretical amount of $CO_2$ taken up (% $CO_2$) was calculated. The volume of $CO_2$ taken up by the amine/amidine solution (V) was calculated from eq. 1, where $V_{blank}$ is the amount of volume decrease in the burette when the flask contained only $CO_2$ and $V_{obs}$ is the total volume decrease measured by the burette.

$$V=(V_{obs}-V_{blank}) \quad (1)$$

The theoretical volume of $CO_2$ ($V_{P,T}$) taken up by M moles of amidine/amine at a known T (K) and P (Torr), assuming complete conversion to amidinium carbamate, was calculated using eq 2.

$$V_{P,T}=[22.4\times(760/P)\times(T/273.15)]\times M \quad (2)$$

Then, $$\%\ CO_2=[V/V_{P,T}]\times 100 \quad (3)$$

The % $CO_2$ values of hexylamine (5), E+5, C+2 and E+6 are shown below for 3 separate experiments. The average is reported in the main text.

| | % $CO_2$ of hexylamine (5) | | | |
|---|---|---|---|---|
| time (min) | sample 1 | sample 2 | sample 3 | average 1-3 |
| 0 | 0 | 0 | 0 | 0 |
| 1 | 39 | 43 | 43 | 41 |
| 2 | 45 | 46 | 44 | 45 |
| 3 | 47 | 47 | 46 | 47 |
| 5 | 48 | 47 | 46 | 47 |
| 10 | 48 | 47 | 47 | 47 |
| 15 | 48 | 47 | 47 | 47 |
| 20 | 48 | 47 | 47 | 47 |
| 25 | 48 | 47 | 47 | 47 |
| 30 | 48 | 47 | 47 | 47 |

| | % $CO_2$ of E + 5 | | | |
|---|---|---|---|---|
| time (min) | sample 1 | sample 2 | sample 3 | average 1-3 |
| 0 | 0 | 0 | 0 | 0 |
| 1 | 41 | 40 | 32 | 38 |
| 2 | 68 | 57 | 47 | 57 |
| 3 | 82 | 71 | 63 | 72 |
| 5 | 91 | 84 | 81 | 85 |
| 10 | 104 | 99 | 96 | 100 |
| 15 | 106 | 104 | 102 | 104 |
| 20 | 108 | 109 | 106 | 108 |
| 25 | 108 | 110 | 108 | 109 |
| 30 | 108 | 111 | 109 | 110 |
| 35 | 108 | 112 | 109 | 110 |
| 40 | 108 | 113 | 110 | 110 |
| 45 | 108 | 114 | 110 | 111 |
| 50 | 108 | 114 | 110 | 111 |
| 55 | 108 | 115 | 110 | 111 |
| 60 | 108 | 115 | 110 | 111 |

| | % $CO_2$ of C + 2 | | | |
|---|---|---|---|---|
| time (min) | sample 1 | sample 2 | sample 3 | average 1-3 |
| 0 | 0 | 0 | 0 | 0 |
| 1 | 73 | 66 | 75 | 71 |
| 2 | 85 | 84 | 87 | 85 |
| 3 | 90 | 90 | 94 | 91 |
| 4 | 94 | 91 | 95 | 93 |
| 5 | 96 | 94 | 97 | 96 |
| 10 | 97 | 96 | 99 | 98 |
| 15 | 101 | 99 | 102 | 101 |
| 20 | 103 | 99 | 103 | 102 |
| 25 | 103 | 100 | 104 | 102 |
| 30 | 104 | 101 | 104 | 103 |
| 35 | 104 | 101 | 104 | 103 |
| 40 | 105 | 101 | 104 | 103 |
| 45 | 105 | 101 | 105 | 103 |
| 50 | 105 | 101 | 105 | 104 |
| 55 | 105 | 101 | 105 | 104 |
| 60 | 106 | 101 | 105 | 104 |

| time (min) | % $CO_2$ of E + 6 sample 1 | sample 2 | sample 3 | average 1-3 |
|---|---|---|---|---|
| 0 | 0 | 0 | 0 | 0 |
| 1 | 29 | 27 | 17 | 24 |
| 2 | 47 | 45 | 33 | 42 |
| 3 | 52 | 53 | 42 | 49 |
| 4 | 59 | 59 | 51 | 56 |
| 5 | 66 | 63 | 55 | 61 |
| 10 | 69 | 70 | 67 | 68 |
| 15 | 71 | 72 | 71 | 71 |
| 20 | 72 | 75 | 72 | 73 |
| 25 | 73 | 76 | 72 | 73 |
| 30 | 73 | 76 | 73 | 74 |
| 35 | 73 | 76 | 73 | 74 |
| 40 | 73 | 76 | 73 | 74 |
| 45 | 73 | 75 | 72 | 73 |
| 50 | 73 | 75 | 72 | 73 |
| 55 | 72 | 75 | 72 | 73 |
| 60 | 72 | 75 | 72 | 73 |

Example 9

UV-Vis Spectroscopic Measurements

An aliquot of a methanol solution of DAPNE was transferred into a sample vial and the methanol was removed by blowing $N_2$ gas over it. Then, an aliquot of the solvent of interest was added and stirred until the solid dissolved completely. The concentrations of DAPNE in the solutions were 32-162 μM. The absorption spectra were recorded in a 1-mm pathlength quartz cuvette. The wavelength maxima are collected in the following table:

| solvent | $\lambda_{max}$ (nm) |
|---|---|
| n-heptane | 393[a] |
| n-decane | 396 |
| n-hexylamine (5) | 416 |
| E | 423 |
| E + 5 | 423 |
| toluene | 425[a] |
| THF | 427 |
| ethanol | 431[a] |
| acetone | 433 |
| DBU + 1-hexanol | 437 |
| E5-C | 438 |
| N,N-dimethylformamide (DMF) | 446[a] |
| dimethyl sulfoxide (DMSO) | 456 |
| water | 496[a] |

[a]Data from Richter-Egger, D. L.; Tesfal, A.; Flamm, S. J.; Tucker, S. A. *J. Chem. Educ.* 2001, 78, 1375-1378

The solvatochromic dye, 1-(p-dimethylaminophenyl)-2-nitroethylene (DAPNE), can be used to estimate the polarity of the reversible RTIL systems. Its absorption maximum in E+5 at 423 nm indicates an environment slightly less polar than toluene ($\lambda_{max}$=425 nm). After $CO_2$ exposure, the E5-C absorption shifted to 438 nm, indicating an environment more polar than acetone ($\lambda_{max}$=433 nm) and less polar than N,N-dimetylformamide (DMF) ($\lambda_{max}$=446 nm). In general, E5-C appears to be less polar than other ionic liquids. For example, 1-butyl-3-methyl imidazolium hexafluorophosphate is much more polar than DMF based upon $E_T(30)$ values.

Chiral Amino Alcohol Systems

Absorption maxima ($\lambda_{max}$) of 2.4 mM DAPNE in various solvents and RTILs.

| solvent | $\lambda_{max}$ (nm) |
|---|---|
| n-heptane | 393 |
| n-decane | 396 |
| C8/Hex | 423 |
| C8/ValOH | 424 |
| C8/IleC$_1$ | 425 |
| Toluene | 425 |
| THF | 427 |
| Acetone | 433 |
| C8-Hex-C | 438 |
| C8-ValOH-C | 443 |
| C8-IleC1-C | 443 |
| DMF | 446 |

Example 10

NMR Spectroscopy

Measured quantities of amidine and amine were dissolved in a known volume of $CDCl_3$. Alternatively, $CO_2$ and $N_2$ were bubbled through the solutions for 30 min at room temperature. At the end of each bubbling period with one gas, NMR spectra were recorded. For the experiment leading to FIG. 4, the $N_2$ bubbling times were 60 min.

Figure 4:
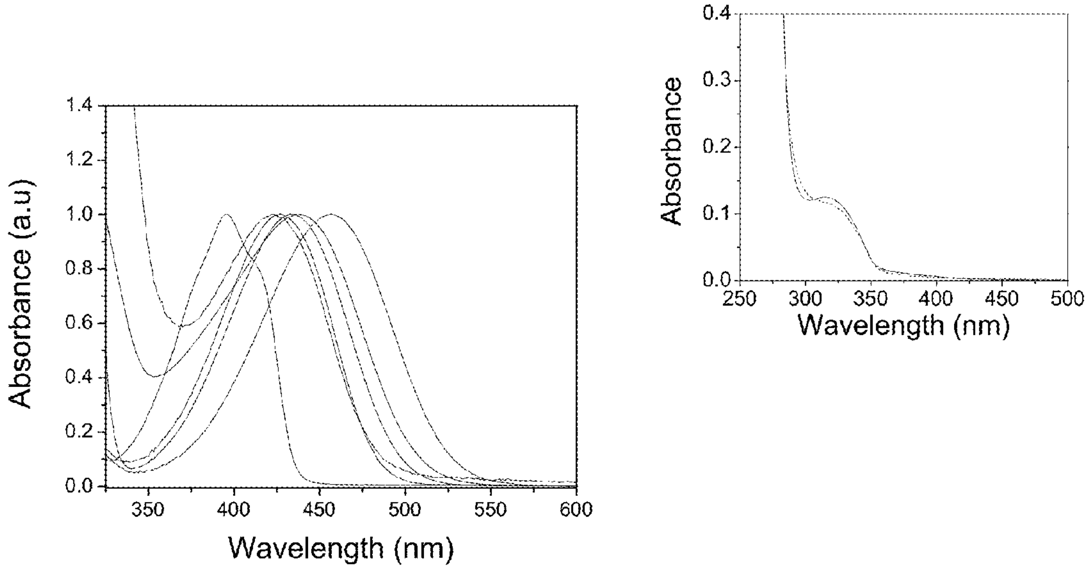
FIG. 4 depicts (i) Normalized UV-vis absorption spectra of the polarity-sensitive dye, DAPNE (1-(p-Dimethylaminophenyl)-2-nitroethylene), in (from left to right) decane, E+5, THF, acetone, E5-C, and DMSO and (ii) UV-vis spectra of E+5 (neat, solid line) and E5-C (neat, dashed line) in a 1 mm pathlength cuvette.
Figure 5:
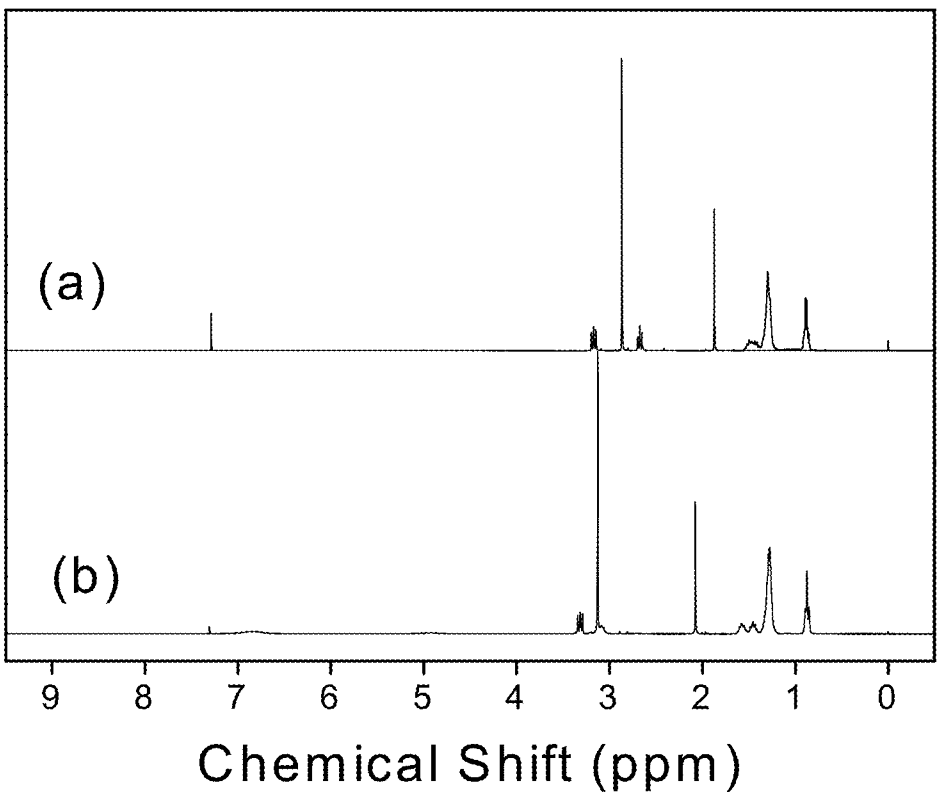
FIG. 5 depicts $^1$H-NMR spectra of 175 mM (a) C8/hexylamine and (b) C8/hexylamine+$CO_2$ in $CDCl_3$.
Figure 7:
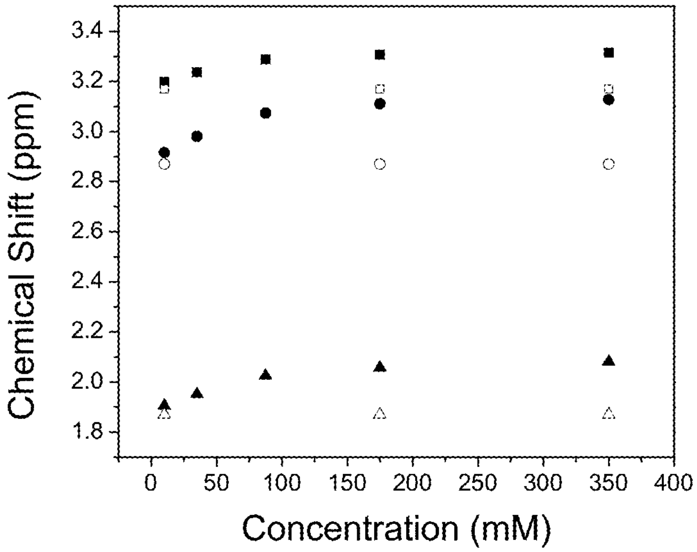
FIG. 7 depicts the chemical shifts of $C\underline{H_2}N{=}C{-}N$ (●, ○), $(N{=}C{-}N(C\underline{H_3})_2)$ (▲, Δ), and $(N{=}C(C\underline{H_3}){-}N)$ (■, □) protons of different concentrations of E+5 (opened symbols) and E5-C (closed symbols) in $CDCl_3$.
Figure 8:
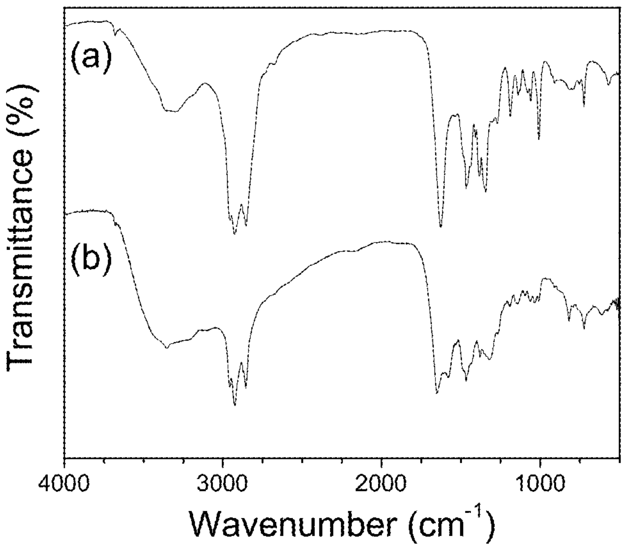
FIG. 8 depicts vertically offset IR spectra of (a) E+5 (neat) and (b) E5-C (neat). Samples were sandwiched between NaCl plates.
Figure 9:
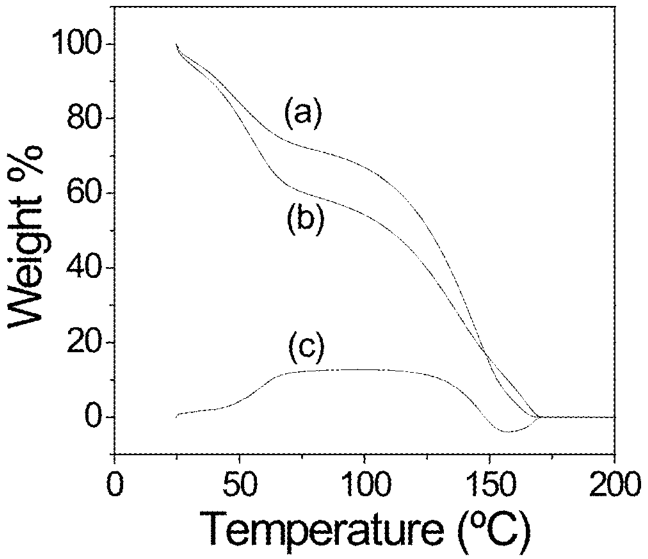
FIG. 9 depicts TGA curves for samples of neat (a) E+5 and (b) E5-C heated from room temperature. Curve (c) is curve (a) minus curve (b).
Figure 15:
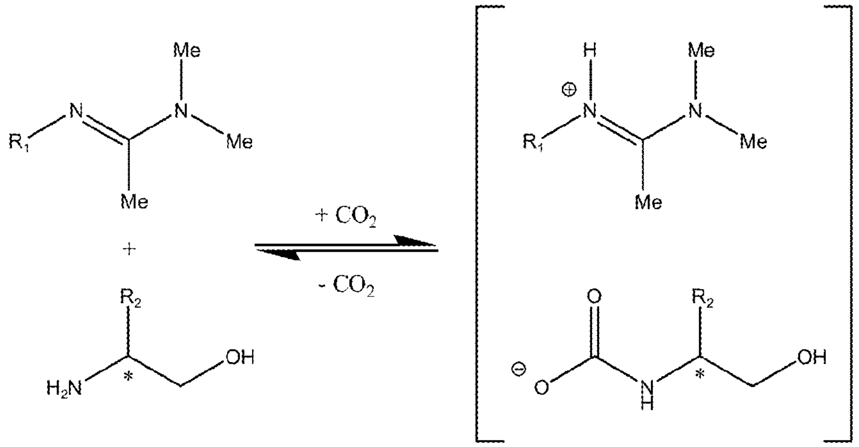
FIG. 15 depicts selected examples of amidines, amino alcohols, and the related RTILs according to the present invention, and a scheme for the associated chemical equilibrium with carbon dioxide as the dissolved gas.
Figure 16:
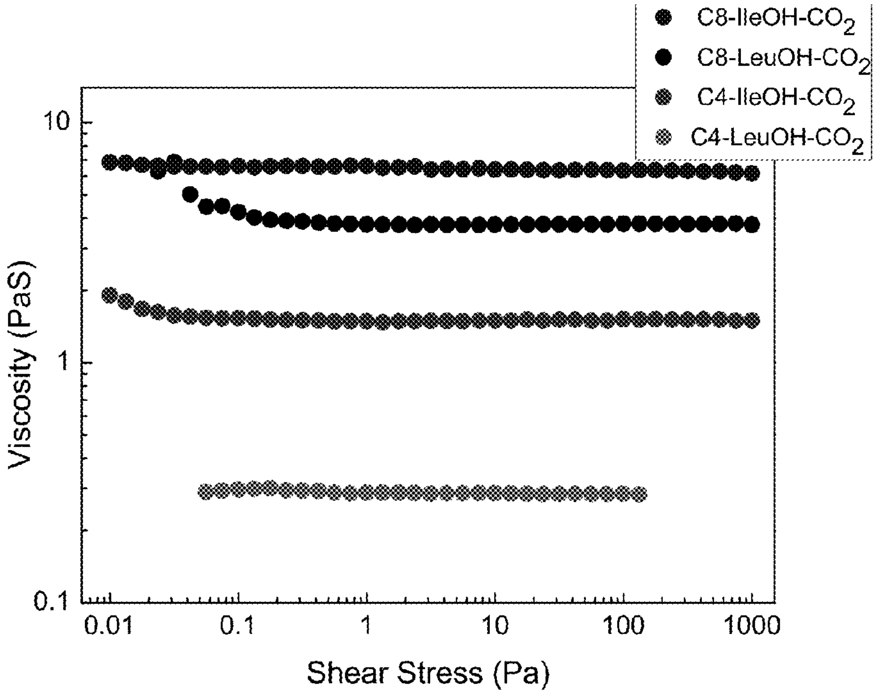
FIG. 16 depicts measured viscosities for various RTILs of the present invention derived from an amidine, amino alcohol, and carbon dioxide. The acronyms used are as defined in FIG. 15.
Figure 17:
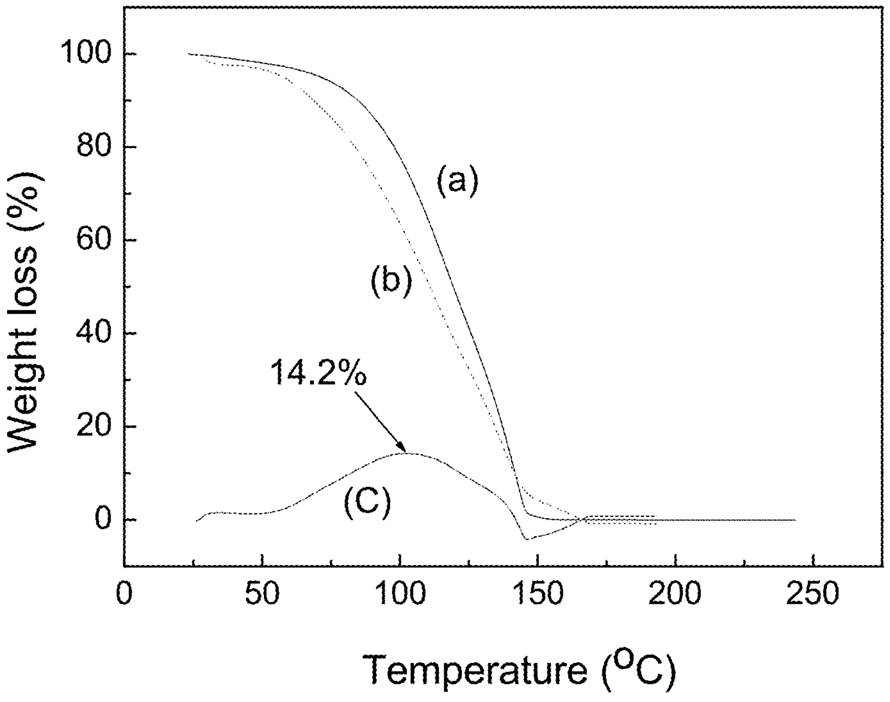
FIG. 17 depicts TGA curves for C6/leucinol before (a) and after (b) $CO_2$ exposure. Both were heated from room temperature. Curve (c) is curve (a) minus curve (b).
Figure 18:
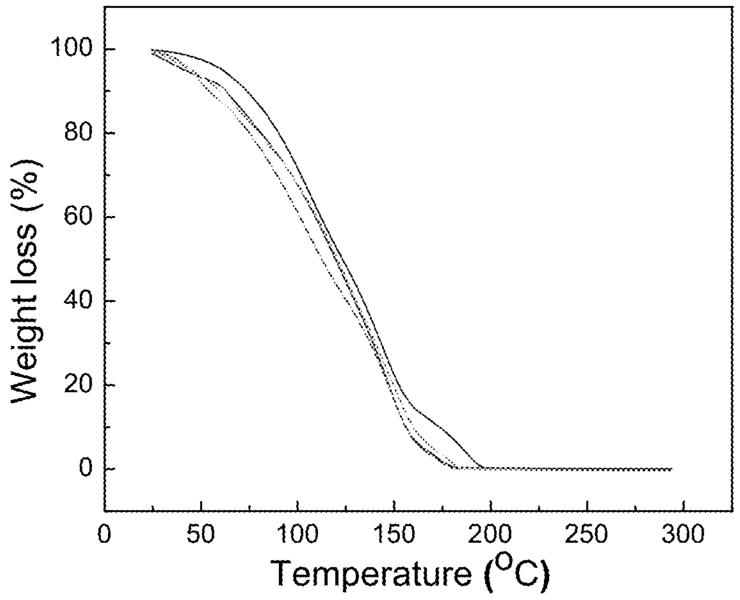
FIG. 18 depicts TGA curves for C8/ProOH (blue curve), C8/IleOH (green curve), C8/LeuOH (red curve) and C8/ValOH (grey curve) after $CO_2$ exposure, heated from room temperature.

The chemical shifts of selected $^1H$ and $^{13}C$ resonances in NMR spectra of Ln-C, but not of the corresponding nuclei in the L+n mixtures, were sensitive to concentration in the range explored, 10-350 mM. A detailed study of this concentration effect was conducted in $CDCl_3$ solutions of the E+5/E5-C system (FIG. 4). The nuclei of E most affected are the protons of the geminal N-dimethyl groups (N═C—N($\underline{CH_3}$)$_2$), the C-methyl protons (N═C($\underline{CH_3}$)—N), the α-methylene protons (—$\underline{CH_2}$N═C—N), and the amidine carbon atom (N═$\underline{C}$($CH_3$)—N). Upon addition of $CO_2$ to solutions of 10 mM E+5, small shifts were observed, but the system had the same spectral features as in the absence of $CO_2$. However, infrared spectral studies conducted with a different amidine-amine pair at 10 mM, showing the presence of the distinctive IR stretching frequencies of amidinium and carbamate, and our previous NMR study of the concentration dependence on chemical shifts of protons and carbon atoms in alkylammonium alkylcarbamates provide strong indirect evidence that E5-C was present after bubbling $CO_2$ even through the 10 mM solution. The shifts, primarily to lower field, increased with increasing solute concentrations upon addition of $CO_2$ and reached plateau values at ca. 100 mM. By bubbling $N_2$ gas through the solutions with higher concentrations of E5-C (N.B. 175 mM; FIG. 4), the proton signals could be returned to their E+5 values; the system was cycled between E+5 and E5-C, with little or no degradation of the sample.

Example 11

IR Spectroscopy

Formation of amidinium carbamate is also evident from the FT-IR spectra of E+5 and E5-C. After $CO_2$ bubbling, the N═C stretching frequencies of E+5 at 1629 $cm^{-1}$ were replaced by bands for E5-C at 1646 and 1575 $cm^{-1}$ which can be assigned to protonated amidine and carbamate stretches.

Example 12

Thermogravimetric Analysis (TGA)

Results from TGA measurements of E+5 and E5-C are included here as an example (FIG. 2). The plateau above 50° C. corresponds to a loss of 12.4% sample weight, in excellent agreement with the calculated $CO_2$ weight loss, 12.8%. The TGA measurements also indicate that some of the amine and amidine components are being evaporated and entrained in the nitrogen wind which the samples experience during the experiments. Regardless, it should be possible to employ the RTIL amidinium carbamates above room temperature while retaining their reversibility with the non-ionic components in a closed vessel.

Example 13

Room-Temperature Ionic Liquids (RTILs) Comprising Amidines and Chiral Amino Alcohols Remarkably, we have discovered room-temperature chiral amidinium carbamate ionic liquids derived from amidines and amino-acid alcohols. The major advantages of this system are chiral, reversible, easy preparation, less sensitive to water and further modifiable for specific task. They are prepared by exposing a 1:1 mixture of an easily synthesized amidine (N'-alkyl-N,N-dimethylacetamidine; L) and an amino alcohol (A), obtained from reduction of naturally occurring amino acid, to an atmosphere of $CO_2$ (C). All of the L/A combinations are liquids at room temperature, and maintain liquid state even at far below 0° C. In addition, L-A-C ionic liquids are able to return to non-ionic state after bubbling inert gas, ($N_2$ or argon), and heating around 50° C. for a more rapid reversion. Amino alcohols comprise chiral centers, modifiable hydroxyl group and may be biodegradable. Six amino alcohols derived from naturally occurring amino acids and one commercially available amino alcohol with two chiral centers, (1S,2S)-norephedrine were studied. The presence of a second chiral center in the amino alcohol may increase the ability of the chiral L/A phase to act as chiral inductor for guest reactions or in separations.

Materials.

Unless stated otherwise, all reagents were used as received. L-Proline (Pro; 99%), L-Leucine (Leu; 99%), L-Isoleucine (Ile; 99%), L-Methionine (Met; 98.5%), L-Phenylalanine (Phe; 98.5%) were from Acros; Triethylamine (99.9%) was from Alfa Aesor; L-Valine (Val; 98%), (15, 25)-Norephedrine (Nor; 99%), n-Decane (99%) and Lithium aluminium hydride ($LiAlH_4$; 95%) were from Aldrich. Methanol (Aldrich, 99.8%) was dried by Vogel's method. Toluene (Aldrich, 99.9%) was dried by refluxing over sodium metal for 5 h, followed by distillation. Tetrohydrofuran (Acros, 99.9%) was dried by refluxing over sodium metal, followed by distillation. Carbon dioxide gas, generated by warming dry-ice, was dried by passing it through a tube filled with indicating Drierite.

Instrumentation.

NMR spectra (referenced to internal tetramethylsilane (TMS) for $^1H$ and to $CDCl_3$ for $^{13}C$) were recorded on a Varian 300 MHz spectrometer interfaced to a Sparc UNIX computer using Mercury software. IR spectra were obtained on a Perkin-Elmer Spectrum One FTIR spectrometer interfaced to a PC, using an attenuated total reflection accessory or NaCl plates. UV-Vis spectra were recorded on a Varian CARY 300 Bio UV-Visible spectrophotometer in Hellma quartz cells with 0.1 mm path lengths. Thermal gravimetric analysis (TGA) measurements were performed under a nitrogen atmosphere at a 5° C./min heating rate on a TGA 2050 thermogravimetric analyzer (TA Instruments) interfaced to a computer. Gas chromatographic (GC) analyses were performed Hewlett-Packard 5890A gas chromatograph equipped with flame ionization detectors and a DB-5 (15 m×0.25 mm) column (J & W Scientific, Inc.). GC-MS measurements were obtained on a SHIMADZU GC-17A gas chromatograph connected SHIMADZU QP-5000 mass spectrometer instrument using a 0.25 μm SGE BPX5 (15 m×0.25 mm) column and a flame ionization detector. Optical rotations were recorded on a Rudolph Instruments Digi-Pal 781 automatic polarimeter at 589 nm in Hellma quartz cells with 0.1 mm path lengths. Conductivity was measured with a YSI model 31 conductivity meter. The conductivity value was calibrated by various concentration of standard KCl solution ($H_2O$, Millipore, 18.3 mΩ).

Syntheses.

The procedure for synthesis of the amino alcohols is presented in detail for L-Leucinol; minor variations were adopted for the other amino alcohols.

L-Leucinol (LeuOH).

Ten grams of L-Leucine (76.2 mmol) was suspended in 100 mL of THF under the nitrogen atmosphere. The suspension was cooled in the ice bath and 4 g of lithium aluminum hydride (100 mmol) was added over a 30 min period. After the addition was complete, the ice bath was removed and the reactant was warmed to room temperature and then refluxed for 24 hours under nitrogen. The reactant was quenched with water (4 mL), then aqueous 15% of sodium hydroxide (4 mL), and water 12 mL. The solution was stirred for 30 min and white precipitate is filtrated. The filter cake was washed with Dichloromethane and the combined organic layer was dried with sodium sulfate, and concentrated under reduced pressure (8.7 g., 97%). The L-leucinol was isolated by distillation. Bp 90° C. (0.9 mm) lit. 64-65° C. (1.5 mm) Yield 5.3 g (59.5%) colorless liquid was obtained. 98% (GC). $^1H$ NMR: δ 3.56 and 3.23 (d-d and t, 2H, $CH_2$—OH); 3.29 (m, 1H, $H_2N$—C*H) 1.8-2.4 (br, 3H, $NH_2$ and OH) 1.68 (m, 1H, $CH_2$—$CH(CH_3)_2$); 1.21 (t, 2H, C*H—$CH_2$—CH); 0.89-0.94 (m, 6H, $CH(CH_3)_2$). $^{13}C$ NMR: δ 67.12, 50.83, 43.68, 24.89, 23.58, 22.38.

L-Prolinol (ProOH).

Yield: 48.0% yellowish clear liquid; 99% (GC). Bp 46-47° C., (0.2 mm); lit. 89° C., (6 mm); 1H NMR: δ 3.22-3.58 (m, 5H, —NH—C*H—$CH_2$—OH); 2.90 (t, 2H, —$CH_2$—$CH_2$—NH—); 1.65-1.88 and 1.34-1.46 (m, 4H, $CH_2$—$CH_2$—C*H). $^{13}C$ NMR: δ 64.90, 59.92, 46.50, 27.65, 26.01.

L-Valinol (ValOH).

Yield: 50.2% colorless clear solid; 98% (GC). Bp 38-39° C., (0.15 mm); lit. 55-57° C., (2 mm); $^1H$ NMR: δ 3.64 and 3.29 (d-d and t, 2H, $CH_2$—OH), 2.56 (m, 1H, $H_2N$—C*H); 1.7-2.2 (br, 3H, $NH_2$ and OH); 1.57 (m, 1H, C*H—CH $(CH_3)_2$); 0.92 (m, 6H, $CH(CH_3)_2$). $^{13}C$ NMR: δ 64.89, 58.64, 31.71, 19.48, 18.56.

L-Isoleucinol (IleOH).

Yield: 53.9% colorless solid was obtained. 98% (GC). Bp 61° C. (0.5 mm), mp 32.5-37.3° C. lit. Bp 100-101° C. (5 mm), mp 38-40° C. $^1H$ NMR: δ 3.64 and 3.28 (d-d and t, 2H, $CH_2$—OH); 2.61-2.68 (m, 1H, C*H); 1.48-1.57 (m, 1H, C*H—CH—); 1.12-1.39 (m, 2H, CH—$CH_2$—$CH_3$); 1.87 (br, 3H, $NH_2$ and OH), 0.87-1.12 (m, 6H, $CH(CH_3)$—$CH_2CH_3$). $^{13}C$ NMR: δ 64.52, 57.19, 38.79, 25.50, 15.29, 11.48.

L-Methioninol (MetOH).

Yield: 83% yellowish clear solid was obtained. 99% (GC). $^1$H NMR: δ 3.60 and 3.34 (d-d and q, 2H, $CH_2$—OH); 2.95 (m, 1H, $H_2N$—C*H); 2.62 (m, 2H, $CH_2$—S—$CH_3$); 2.11 (s, 3H, $CH_2$—S—$CH_3$); 2.0-2.3 (br, 3H, $NH_2$ and OH) 1.73 and 1.54 (m, 2H, $CH_2$—$CH_2$—S—$CH_3$). $^{13}$C NMR: δ 66.92, 52.16, 33.83, 31.26, 15.83. GC-MS: Calcd for $C_5H_{13}NOS$, 135. found 136 ($[M+H]^+$).

L-Phenylalaninol (PheOH).

Yield: 2.8 g (62%) colorless clear solid was obtained. 99% (GC). mp 92.5-94.4° C. (lit. 91-93° C.). $^1$H NMR: δ 1.64 (br, 3H, $NH_2$ and OH), 2.53 (d-d, 1H, $CH_2$-Ph), 2.80 (d-d, 1H $CH_2$Ph), 3.12, (m, 1H, NCH), 3.36 (d-d, 1H, $CH_2$O), 3.64 (d-d, 1H, $CH_2$O), 7.18-7.34 (m, 5H, PhH). $^{13}$C NMR: δ138.95, 129.47, 128.85, 126.69, 66.64, 54.43, 41.22.

Results and Discussion

The phase appearances of various L/A combinations at room temperature and −20° C. before and after bubbling $CO_2$ are shown in FIG. 20. Significantly, unlike amino ester/amidine system, all the combinations formed clear, nearly colorless ionic liquids after exposure to $CO_2$ at room temperature, although some of the original mixtures were not fluent liquids. Similarly, all the L-A-C remained liquids even at −20° C. It is likely that the types of cations and anions do not significantly affect the phase appearances in this L/A system. As expected, the L/A mixtures are less viscous than the corresponding L-A-C ionic liquids. Qualitatively, the viscosity of some ionic liquids obtained from PheOH and NorOH, the phenyl-substituted amino alcohols, are higher than those obtained from alkyl-substituted amino alcohols. The presence of hydrogen bonding and other ion interactions might give rise to the high viscosity of ionic liquids (but still maintained their fluidity). In general, the resulting L-A-C ionic liquids are stable at room temperature and one atmosphere of pressure, and the maximum temperature at which L-A-C starts to lose $CO_2$ is ca. 50° C. according to TGA measurements.

The amino alcohol L/A systems appear to tolerate a certain amount (10%) of water in either the neutral or polar state, although the reactions were performed in dry condition. Also, the addition of water to a L/A mixture did not impede the formation of L-A-C upon bubbling $CO_2$ and no precipitate or cloudy appearance was observed.

The formation of amidinium carbamates was confirmed by several measurements, such as % $CO_2$ uptake, FT-IR, TGA, $^1$H and $^{13}$C NMR. The absorption of $CO_2$ by our amino alcohol/amidine systems was quantitatively measured by using a gas burette containing 1 atm pressure of dry $CO_2$ at room temperature. Analysis of Leucinol/C8 and Valinol/C8 showed the rate of $CO_2$ uptaken by these mixtures was fast in first 10 min, and reached the theoretical value 100% at approximately 30 min. The fairly slow absorption of $CO_2$ was observed after 30 min and 10% excess $CO_2$ was uptaken until reaching a plateau after 60 min. The end-point values around 110% indicate both chemically fixed and physically dissolved carbon dioxide. The initial rapid (ca. 100%) absorption corresponds to the complete conversion to RTILs, with excess (ca. 10%) $CO_2$ slowly dissolving into the RTIL phase afterward.

One of the remarkable advantages of amino alcohol L-A-C system is the rapid and quantitative reversibility between nonionic and ionic liquid states. In general, L-A-C ionic liquids could be returned to their non ionic precursor states by simply bubbling $N_2$ or argon at room temperature. Heating the ionic liquids at ca. 50° C. during exposure to $N_2$ or argon increased the speed of the reversal process.

Additional evidence of reversibility was obtained from conductivity measurements. Because viscosity can influence conductivity, the measurements were conducted in $CHCl_3$ solution. The neutral IleOH/C8 mixture had low conductivity. After bubbling $CO_2$ into the IleOH/C8 $CHCl_3$ solution, the conductivity increased rapidly, indicating the formation of the IleOH—C8-C ionic liquid, and reaching a plateau value of 268 μs/cm. When $N_2$ was passed through the solution, the conductivity decreased to 25 μs/cm, consistent with return to the neutral state from the L-C-A ionic liquid.

Ionic liquids are viewed as green alternatives to common volatile organic solvents. Therefore, assessment of their miscibility with other molecular solvents is important, particularly for developing ILs for liquid-liquid extraction processes. The amino alcohol L-A-Cs are miscible with highly polar solvents, such as water, DMSO and ethanol. With low polarity solvents, such as hexane, toluene and diethyl ether, two separate phases were observed, confirming that the L-A-Cs are immiscible with these solvents. The L-A-C ionic liquids prepared from phenyl-substituted amino alcohols (NorOH, PheOH), are immiscible or only partly miscible with dichloromethane and ethyl acetate, while C6-NorOH—C is also only partly miscible with chloroform. The other amino alcohol L-A-Cs appeared to have good miscibility with dichloromethane, ethyl acetate and chloroform.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

We claim:

1. A salt represented by:

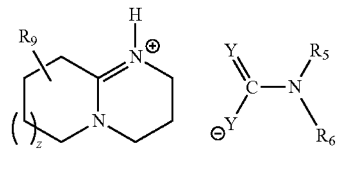

wherein $R_9$ is absent or represents one or more substituents attached to the ring, each of which is independently selected from the group consisting of H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(=O)OR_8$, $—OC(=O)R_8$, $—NR_8C(=O)R_8$, $—C(=O)N(R_8)_2$, $—C(=O)SR_8$, $—SC(=O)R_8$, $—S(=O)R_8$, $—S(=O)_2R_8$, $—S(=O)_2OR_8$, $—C(=O)R_8$, $—C(=NR_8)R_8$, $—C(=S)R_8$, $—C(R_8)=C(R_8)_2$, $—C\equiv CR_8$, $—CH(R_8)_2$, $—C(R_8)_3$, and $—(CH_2)_n—NH_2$;

z is zero or an integer in the range of 1 to 3;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(═O)OR_8$, $—OC(═O)R_8$, $—NR_8C(═O)R_8$, $—C(═O)N(R_8)_2$, $—C(═O)SR_8$, $—SC(═O)R_8$, $—S(═O)R_8$, $—S(═O)_2R_8$, $—S(═O)_2OR_8$, $—C(═O)R_8$, $—C(═NR_8)R_8$, $—C(═S)R_8$, $—C(R_8)═C(R_8)_2$, $—C≡CR_8$, $—CH(R_8)_2$, $—C(R_8)_3$, or $—(CH_2)_n—NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(═O)OR_8$, $—OC(═O)R_8$, $—NR_8C(═O)R_8$, $—C(═O)N(R_8)_2$, $—C(═O)SR_8$, $—SC(═O)R_8$, $—S(═O)R_8$, $—S(═O)_2R_8$, $—S(═O)_2OR_8$, $—C(═O)R_8$, $—C(═NR_8)R_8$, $—C(═S)R_8$, $—C(R_8)═C(R_8)_2$, $—C≡R_8$, $—CH(R_8)_2$, $—C(R_8)_3$, or $—(CH_2)_n—NH_2$;

Y represents independently for each occurrence O or S;

$R_8$ represents independently for each occurrence $—(CH_2)_n—CH_3$, cycloalkyl, aryl, or heteroaryl; and n represents independently for each occurrence an integer in the range 1-10 inclusive.

2. The salt of claim 1, wherein $R_9$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)═C(R_8)_2$, $—C≡CR_8$, $—CH(R_8)_2$, or $—C(R_8)_3$;

$R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)═C(R_8)_2$, $—C≡CR_8$, $—CH(R_8)_2$, or $—C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)═C(R_8)_2$, $—C≡CR_8$, $—CH(R_8)_2$, or $—C(R_8)_3$.

3. The salt of claim 1, wherein $R_9$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$; and $R_6$ represents H, alkyl, fluoroalkyl, cycloalkyl, heterocycloalkyl, $—(CH_2)_n—R_8$, $—CH(R_8)_2$, or $—C(R_8)_3$.

4. The salt of claim 1, wherein $R_9$ represents H, alkyl, fluoroalkyl, cycloalkyl, heterocycloalkyl, $—(CH_2)_n—R_8$, $—CH(R_8)_2$, or $—C(R_8)_3$;

$R_5$ represents H, alkyl, fluoroalkyl, cycloalkyl, heterocycloalkyl, $—(CH_2)_n—R_8$, $—CH(R_8)_2$, or $—C(R_8)_3$;

$R_6$ represents H, alkyl, fluoroalkyl, cycloalkyl, heterocycloalkyl, $—(CH_2)_n—R_8$, $—CH(R_8)_2$, or $—C(R_8)_3$; and Y is O.

5. A salt represented by:

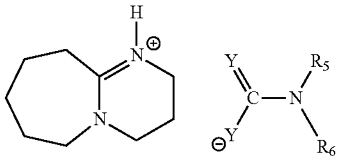

wherein $R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(═O)OR_8$, $—OC(═O)R_8$, $—NR_8C(═O)R_8$, $—C(═O)N(R_8)_2$, $—C(═O)SR_8$, $—S C(═O)R_8$, $—S(═O)R_8$, $—S(═O)_2R_8$, $—S(═O)_2OR_8$, $—C(═O)R_8$, $—C(═NR_8)R_8$, $—C(═S)R_8$, $—C(R_8)═C(R_8)_2$, $—C≡CR_8$, $—CH(R_8)_2$, $—C(R_8)_3$, or $—(CH_2)_n—NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(═O)OR_8$, $—OC(═O)R_8$, $—NR_8C(═O)R_8$, $—C(═O)N(R_8)_2$, $—C(═O)SR_8$, $—S C(═O)R_8$, $—S(═O)R_8$, $—S(═O)_2R_8$, $—S(═O)_2OR_8$, $—C(═O)R_8$, $—C(═NR_8)R_8$, $—C(═S)R_8$, $—C(R_8)═C(R_8)_2$, $—C≡CR_8$, $—CH(R_8)_2$, $—C(R_8)_3$, or $—(CH_2)_n—NH_2$;

Y represents independently for each occurrence O or S;

$R_8$ represents independently for each occurrence $—(CH_2)_n—CH_3$, cycloalkyl, aryl, or heteroaryl; and n represents independently for each occurrence an integer in the range 1-10 inclusive.

6. The salt of claim 5, wherein $R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)═C(R_8)_2$, $—C≡CR_8$, $—CH(R_8)_2$, or $—C(R_8)_3$; and $R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—C(R_8)═C(R_8)_2$, $—C≡CR_8$, $—CH(R_8)_2$, or $—C(R_8)_3$.

7. The salt of claim 5, wherein $R_5$ represents H, alkyl, fluoroalkyl, cycloalkyl, heterocycloalkyl, $—(CH_2)_n—R_8$, $—CH(R_8)_2$, or $—C(R_8)_3$; and $R_6$ represents H, alkyl, fluoroalkyl, cycloalkyl, heterocycloalkyl, $—(CH_2)_n—R_8$, $—CH(R_8)_2$, or $—C(R_8)_3$.

8. The salt of claim 5, wherein $R_5$ represents H, alkyl, fluoroalkyl, cycloalkyl, heterocycloalkyl, $—(CH_2)_n—R_8$, $—CH(R_8)_2$, or $—C(R_8)_3$;

$R_6$ represents H, alkyl, fluoroalkyl, cycloalkyl, heterocycloalkyl, $—(CH_2)_n—R_8$, $—CH(R_8)_2$, or $—C(R_8)_3$; and Y is O.

9. A method of preparing a salt, comprising the step of contacting a gas with a first compound and a second compound, wherein said first compound is represented by

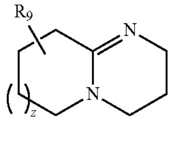

wherein $R_9$ is absent or represents one or more substituents attached to the ring, each of which is independently selected from the group consisting of H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $—(CH_2)_n—R_8$, $—OR_8$, $—N(R_8)_2$, $—SR_8$, $—C(═O)OR_8$, $—OC(═O)R_8$, $—NR_8C(═O)R_8$, $—C(═O)N(R_8)_2$, $—C(═O)SR_8$, —S C(=O)R$_8$, —S(=O)R$_8$, —S(=O)$_2$R$_8$, —S(=O)$_2$OR$_8$, —C(=O)R$_8$, —C(=NR$_8$)R$_8$, —C(=S)R$_8$, —C(R$_8$)=C(R$_8$)$_2$, —C≡CR$_8$, —CH(R$_8$)$_2$, —C(R$_8$)$_3$, and —(CH$_2$)$_n$—NH$_2$;

R$_8$ represents independently for each occurrence —(CH$_2$)$_n$—CH$_3$, cycloalkyl, aryl, or heteroaryl;

n represents independently for each occurrence an integer in the range 1-10 inclusive;

z is zero or an integer in the range of 1 to 3; and said second compound is represented by

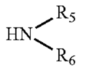

wherein

R$_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —(CH$_2$)$_n$—R$_8$, —OR$_8$, —N(R$_8$)$_2$, —SR$_8$, —C(=O)OR$_8$, —OC(=O)R$_8$, —NR$_8$C(=O)R$_8$, —C(=O)N(R$_8$)$_2$, —C(=O)SR$_8$, —S C(=O)R$_8$, —S(=O)R$_8$, —S(=O)$_2$R$_8$, —S(=O)$_2$OR$_8$, —C(=O)R$_8$, —C(=NR$_8$)R$_8$, —C(=S)R$_8$, —C(R$_8$)=C(R$_8$)$_2$, —C≡CR$_8$, —CH(R$_8$)$_2$, —C(R$_8$)$_3$, or —(CH$_2$)$_n$—NH$_2$;

R$_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —(CH$_2$)$_n$—R$_8$, —OR$_8$, —N(R$_8$)$_2$, —SR$_8$, —C(=O)OR$_8$, —OC(=O)R$_8$, —NR$_8$C(=O)R$_8$, —C(=O)N(R$_8$)$_2$, —C(=O)SR$_8$, —S C(=O)R$_8$, —S(=O)R$_8$, —S(=O)$_2$R$_8$, —S(=O)$_2$OR$_8$, —C(=O)R$_8$, —C(=NR$_8$)R$_8$, —C(=S)R$_8$, —C(R$_8$)=C(R$_8$)$_2$, —C≡CR$_8$, —CH(R$_8$)$_2$, —C(R$_8$)$_3$, or —(CH$_2$)$_n$—NH$_2$;

R$_8$ represents independently for each occurrence —(CH$_2$)$_n$—CH$_3$, cycloalkyl, aryl, or heteroaryl;

n represents independently for each occurrence an integer in the range 1-10 inclusive; and said gas is represented by:

Y=X=Y wherein

X represents C or N; and

Y represents independently for each occurrence O or S.

10. A method comprising the step of contacting a first gas with an ionic liquid, thereby generating a second gas; wherein said ionic liquid is represented by:

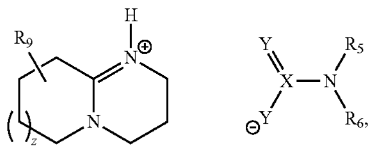

wherein said first gas is an inert gas;

said second gas is CO$_2$ or CS$_2$;

R$_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —(CH$_2$)$_n$—R$_8$, —OR$_8$, —N(R$_8$)$_2$, —SR$_8$, —C(=O)OR$_8$, —OC(=O)R$_8$, —NR$_8$C(=O)R$_8$, —C(=O)N(R$_8$)$_2$, —C(=O)SR$_8$, —S C(=O)R$_8$, —S(=O)R$_8$, —S(=O)$_2$R$_8$, —S(=O)$_2$OR$_8$, —C(=O)

R$_8$, —C(=NR$_8$)R$_8$, —C(=S)R$_8$, —C(R$_8$)=C(R$_8$)$_2$, —C≡CR$_8$, —CH(R$_8$)$_2$, —C(R$_8$)$_3$, or —(CH$_2$)$_n$—NH$_2$;

R$_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —(CH$_2$)$_n$—R$_8$, —OR$_8$, —N(R$_8$)$_2$, —SR$_8$, —C(=O)OR$_8$, —OC(=O)R$_8$, —NR$_8$C(=O)R$_8$, —C(=O)N(R$_8$)$_2$, —C(=O)SR$_8$, —S C(=O)R$_8$, —S(=O)R$_8$, —S(=O)$_2$R$_8$, —S(=O)$_2$OR$_8$, —C(=O)R$_8$, —C(=NR$_8$)R$_8$, —C(=S)R$_8$, —C(R$_8$)=C(R$_8$)$_2$, —C≡CR$_8$, —CH(R$_8$)$_2$, —C(R$_8$)$_3$, or —(CH$_2$)$_n$—NH$_2$;

X represents C;

Y represents independently for each occurrence O or S;

R$_8$ represents independently for each occurrence —(CH$_2$)$_n$—CH$_3$, cycloalkyl, aryl, or heteroaryl;

R$_9$ is absent or represents one or more substituents attached to the ring, each of which is independently selected from the group consisting of H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —(CH$_2$)$_n$—R$_8$, —OR$_8$, —N(R$_8$)$_2$, —SR$_8$, —C(=O)OR$_8$, —OC(=O)R$_8$, —NR$_8$C(=O)R$_8$, —C(=O)N(R$_8$)$_2$, —C(=O)SR$_8$, —S C(=O)R$_8$, —S(=O)R$_8$, —S(=O)$_2$R$_8$, —S(=O)$_2$OR$_8$, —C(=O)R$_8$, —C(=NR$_8$)R$_8$, —C(=S)R$_8$, —C(R$_8$)=C(R$_8$)$_2$, —C≡CR$_8$, —CH(R$_8$)$_2$, —C(R$_8$)$_3$, and —(CH$_2$)$_n$—NH$_2$;

z is zero or an integer in the range of 1 to 3; and n represents independently for each occurrence an integer in the range 1-10 inclusive.

11. A method of removing a gas from a mixture, comprising the step of contacting said mixture with a first compound and a second compound, wherein said first compound is represented by

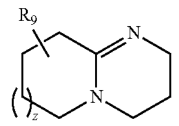

wherein

R$_9$ is absent or represents one or more substituents attached to the ring, each of which is independently selected from the group consisting of H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, —(CH$_2$)$_n$—R$_8$, —OR$_8$, —N(R$_8$)$_2$, —SR$_8$, —C(=O)OR$_8$, —OC(=O)R$_8$, —NR$_8$C(=O)R$_8$, —C(=O)N(R$_8$)$_2$, —C(=O)SR$_8$, —S C(=O)R$_8$, —S(=O)R$_8$, —S(=O)$_2$R$_8$, —S(=O)$_2$OR$_8$, —C(=O)R$_8$, —C(=NR$_8$)R$_8$, —C(=S)R$_8$, —C(R$_8$)=C(R$_8$)$_2$, —C≡CR$_8$, —CH(R$_8$)$_2$, —C(R$_8$)$_3$, or —(CH$_2$)$_n$—NH$_2$;

R$_8$ represents independently for each occurrence —(CH$_2$)$_n$—CH$_3$, cycloalkyl, aryl, or heteroaryl;

n represents independently for each occurrence an integer in the range 1-10 inclusive;

z is zero or an integer in the range of 1 to 3; and said second compound is represented by

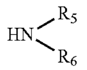

wherein $R_5$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-S\ C(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, $-C(R_8)_3$, or $-(CH_2)_n-NH_2$;

$R_6$ represents H, halogen, alkyl, fluoroalkyl, cycloalkyl, heterocycloalkyl, alkenyl, cycloalkenyl, heterocycloalkenyl, alkynyl, aryl, heteroaryl, aralkyl, heteroaralkyl, $-(CH_2)_n-R_8$, $-OR_8$, $-N(R_8)_2$, $-SR_8$, $-C(=O)OR_8$, $-OC(=O)R_8$, $-NR_8C(=O)R_8$, $-C(=O)N(R_8)_2$, $-C(=O)SR_8$, $-S\ C(=O)R_8$, $-S(=O)R_8$, $-S(=O)_2R_8$, $-S(=O)_2OR_8$, $-C(=O)R_8$, $-C(=NR_8)R_8$, $-C(=S)R_8$, $-C(R_8)=C(R_8)_2$, $-C\equiv CR_8$, $-CH(R_8)_2$, $-C(R_8)_3$, or $-(CH_2)_n-NH_2$;

$R_8$ represents independently for each occurrence cycloalkyl, aryl, or heteroaryl;

n represents independently for each occurrence an integer in the range 1-10 inclusive; and said gas is represented by:

$$Y=X=Y$$

wherein

X represents C or N; and

Y represents independently for each occurrence O or S.

* * * * *